(12) United States Patent
Shin et al.

(10) Patent No.: US 10,786,169 B2
(45) Date of Patent: Sep. 29, 2020

(54) BIO-PROCESSOR FOR MEASURING EACH BIOLOGICAL SIGNALS AND WEARABLE DEVICE HAVING THE SAME

(71) Applicant: Samsung Electronics Co., Ltd., Suwon-si, Gyeonggi-do (KR)

(72) Inventors: Seung-Chul Shin, Seoul (KR); Gye Soo Koo, Gunpo-si (KR); Se-Hoon Lim, Suwon-si (KR); Hee-Jae Jo, Suwon-si (KR); Hyung Jong Ko, Seongnam-si (KR); Yong In Park, Seoul (KR); Seoung Jae Yoo, Seongnam-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 983 days.

(21) Appl. No.: 15/332,265

(22) Filed: Oct. 24, 2016

(65) Prior Publication Data
US 2017/0172448 A1    Jun. 22, 2017

(30) Foreign Application Priority Data
Dec. 21, 2015  (KR) ........................ 10-2015-0183032

(51) Int. Cl.
*A61B 5/0408*        (2006.01)
*A61B 5/053*         (2006.01)
(Continued)

(52) U.S. Cl.
CPC ........ *A61B 5/04085* (2013.01); *A61B 5/0022* (2013.01); *A61B 5/0464* (2013.01); *A61B 5/053* (2013.01); *A61B 5/0533* (2013.01); *A61B 5/681* (2013.01); *G16H 10/60* (2018.01); *H04B 1/385* (2013.01); *A61B 5/0245* (2013.01); *A61B 5/02405* (2013.01); *A61B 5/0537* (2013.01); *A61B 5/165* (2013.01); *A61B 5/4809* (2013.01); *A61B 5/746* (2013.01);
(Continued)

(58) Field of Classification Search
CPC ............ A61B 5/04001; A61B 5/04002; A61B 5/0402; A61B 5/0408; A61B 5/04087; A61B 5/040284; A61B 5/053; A61B 5/0531; A61B 5/0533; A61B 5/0537; A61B 5/681
See application file for complete search history.

(56) References Cited

U.S. PATENT DOCUMENTS 4,448,203 A    5/1984 Williamson et al.
4,669,477 A    6/1987 Ober
(Continued)

*Primary Examiner* — Eun Hwa Kim
(74) *Attorney, Agent, or Firm* — Volentine, Whitt & Francos, PLLC

(57) ABSTRACT

A wearable device includes a case, a bio-processor embedded in the case, and a plurality of electrodes connected to the bio-processor. The bio-processor is configured to selectively and respectively operate the electrodes as sensing electrodes and sourcing electrodes in response to a selection signal. The selected one/ones of the electrodes operated as sensing electrodes which pick up a biological signal from (e.g. biological activity or a biological condition of) the wearer. The selected one/ones of the electrodes operated as sourcing electrodes supply current to the wearer regulated to cause the desired biological signal to be picked up by the sensing electrode(s).

17 Claims, 19 Drawing Sheets

(51) Int. Cl.
*A61B 5/0464* (2006.01)
*G16H 10/60* (2018.01)
*A61B 5/00* (2006.01)
*H04B 1/3827* (2015.01)
*A61B 5/024* (2006.01)
*A61B 5/0245* (2006.01)
*A61B 5/16* (2006.01)
*G16H 40/20* (2018.01)
*G16H 40/63* (2018.01)
*G16H 40/67* (2018.01)

(52) U.S. Cl.
CPC ... *A61B 2560/0214* (2013.01); *A61B 2562/04* (2013.01); *G16H 40/20* (2018.01); *G16H 40/63* (2018.01); *G16H 40/67* (2018.01)

(56) References Cited

U.S. PATENT DOCUMENTS

| | | | |
|---|---|---|---|
| 4,993,423 A | 2/1991 | Stice | |
| 6,516,289 B2 | 2/2003 | David | |
| 6,520,905 B1 | 2/2003 | Surve et al. | |
| 6,625,487 B2 | 9/2003 | Herleikson | |
| 6,636,763 B1 | 10/2003 | Junker et al. | |
| 7,925,340 B2 * | 4/2011 | Masuo | A61B 5/0537 600/547 |
| 8,160,689 B2 | 4/2012 | Jadidi | |
| 8,311,605 B2 | 11/2012 | Wilder-Smith et al. | |
| 9,053,308 B2 | 6/2015 | Lange | |
| 9,138,579 B2 | 9/2015 | Wolpaw et al. | |
| 2003/0176808 A1 * | 9/2003 | Masuo | A61B 5/0537 600/547 |
| 2010/0033303 A1 | 2/2010 | Dugan et al. | |
| 2014/0051941 A1 | 2/2014 | Messerschmidt | |
| 2015/0157220 A1 * | 6/2015 | Fish | A61B 5/02055 600/301 |
| 2016/0070393 A1 * | 3/2016 | Sharma | A61B 5/002 345/174 |
| 2016/0073914 A1 * | 3/2016 | Lapetina | A61B 5/6824 600/384 |
| 2016/0192856 A1 * | 7/2016 | Lee | A61B 5/6804 600/384 |
| 2016/0287172 A1 * | 10/2016 | Morris | A61B 5/04085 |

* cited by examiner

BIA SIGNAL MEASURE

ECG SIGNAL MEASURE

GSR SIGNAL MEASURE

BIO-PROCESSOR FOR MEASURING EACH BIOLOGICAL SIGNALS AND WEARABLE DEVICE HAVING THE SAME

PRIORITY STATEMENT

This application claims priority under 35 U.S.C. § 119(a) from Korean Patent Application No. 10-2015-0183032 filed on Dec. 21, 2015, the disclosure of which is hereby incorporated by reference in its entirety.

BACKGROUND

The present inventive concept relates to a bio-processor, and to a wearable device including a bio-processor.

An electrocardiogram (ECG) be generated by various methods and then analyzed to check the state of health of a person's heart. In general, the ECG is generated using a high-precision voltage measuring device and ten or more medical-purpose electrodes attached to a person's body, and is analyzed by a doctor. More specifically, ten or more electrodes are attached to a patient's torso and limbs in a predetermined order, electrical activity of the heart is picked up by the electrodes and converted into an ECG signal, the ECG signal is displayed as a graph referred to as the ECG, and the ECG is directly analyzed by a doctor.

A growing technology in recent years is the technology of wearable devices which measure biological activity of a person wearing the device and which are used to monitor a state of health of the person according to such measurements of biological activity. These wearable devices can generate an ECG signal at various places on the human body and process the ECG signal using hardware such as a digital signal processor. However, the end user may be the party responsible for setting the positions of the electrodes for generating the ECG signal, and may not be skilled at positioning the electrodes. Therefore, an ECG signal processed by the digital signal processor may not accurately reveal a state of health of the heart of the user.

SUMMARY

An example of the present inventive concept is a wearable device including a case, a bio-processor embedded in the case, and a plurality of electrodes electrically connected to the bio-processor, and in which the bio-processor is configured to decide, based on a selection signal indicating a type of data desired, which ones of the plurality of electrodes to use as sensing electrodes for sensing a biological signal from a wearer of the device, and in which the bio-processor is configured to decide, based on the selection signal, which ones of the plurality of electrodes to use as sourcing electrodes for supplying current to the wearer of the device.

An example of the present inventive concept is a processor including a plurality of pads each connected to an electrode of a corresponding one of a plurality of electrodes, a controller which receives a selection signal indicating a type of a biological signal to be sensed, and an electrode control circuit which decides which ones of the plurality of pads to use as sensing pads for sensing a biological signal under the control of the controller operating based on the selection signal, and decides which ones of the plurality of pads to use as sourcing pads for supplying a source current causing the biological signal under the control of the controller.

Another example of the present inventive concept is a wearable device including a case, a bio-processor embedded in the case, and a plurality of electrodes operatively electrically connected to the bio-processor, and in which the bio-processor is configured to select a number of the electrodes for use in sensing activity at an anatomical region of a user who wears the device, based on a selection signal indicative of a type of biological signal to be produced from the activity, and to enable the selected electrodes to sense said activity and produce the biological signal.

Yet another example of the present inventive concept is a wearable device including a jacket securable to an anatomical region of a user of the device, a processor disposed within the jacket, a power source integral with the jacket, and at least three electrodes integral with the jacket and electrically connected to the processor, and in which the processor is operatively electrically connected to the power source and to the electrodes and is configured to operate the device selectively in a plurality of different modes in response to mode selection signals, respectively. In one of the modes a first group of the electrodes is used to produce a signal representative of biological data of a first type and respective ones of the electrodes constituting the first group are electrically connected to the power source so as to serve as source electrodes through which current is supplied to the anatomical region. In another of the modes a group of the electrodes, different from the first group, is used to produce a signal representative of biological data of a second type different than the first type.

BRIEF DESCRIPTION OF THE DRAWINGS

These and/or other aspects and advantages of the present general inventive concept will become apparent and more readily appreciated from the following description of examples thereof, taken in conjunction with the accompanying drawings of which.

DETAILED DESCRIPTION

Figure 1:
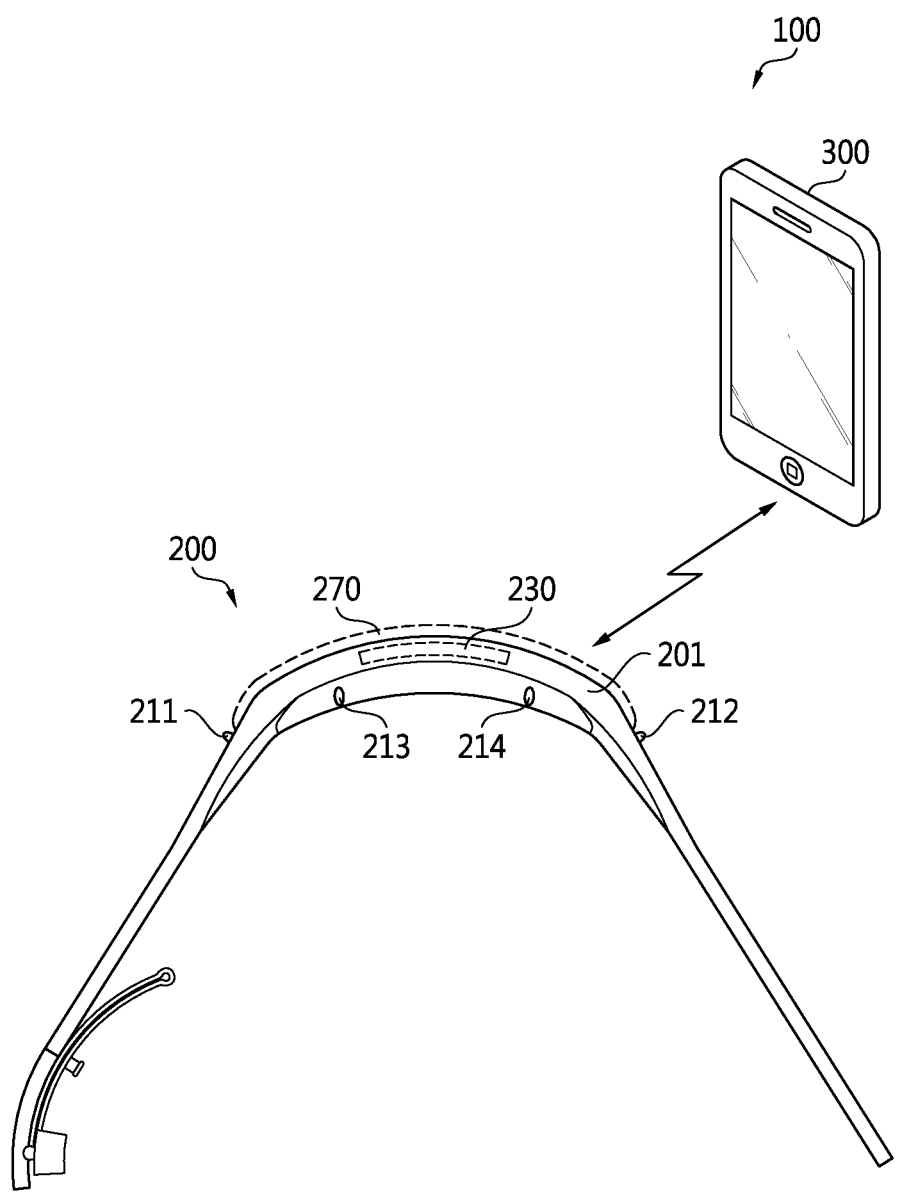
FIG. 1 is a perspective view of a data processing system including a wearable device and a smart phone according to an example of the present inventive concept.

Reference will now be made in detail to examples of the present general inventive concept, which are illustrated in the accompanying drawings, and wherein like reference numerals designate like elements throughout. The examples are described below in order to explain the present general inventive concept by referring to the figures.

As is traditional in the field of the inventive concept, the examples may be described and illustrated in terms of blocks which carry out a described function or functions. These blocks, which may be referred to herein as units or modules or the like, are physically implemented by analog and/or digital circuits such as logic gates, integrated circuits, microprocessors, microcontrollers, memory circuits, passive electronic components, active electronic components, optical components, hardwired circuits and the like, and may optionally be driven by firmware and/or software. The circuits may, for example, be embodied in one or more semiconductor chips, or on substrate supports such as printed circuit boards and the like. The circuits constituting a block may be implemented by dedicated hardware, or by a processor (e.g., one or more programmed microprocessors and associated circuitry), or by a combination of dedicated hardware to perform some functions of the block and a processor to perform other functions of the block. Each block of the examples may be physically separated into two or more interacting and discrete blocks without departing from the scope of the inventive concept. Likewise, the blocks of the examples may be physically combined into more complex blocks without departing from the scope of the inventive concept.

Furthermore, terminology used herein for the purpose of describing particular examples or embodiments of the inventive concept is to be taken in context. For example, the terms "comprises" or "comprising" when used in this specification specifies the presence of stated features or processes but does not preclude the presence or additional features or processes. The term "operatively connected" may be understood as referring to a connection through electronic means (wiring and/or electronic components) even in the case in which such means allow electrical power through the connection to be cut off in a certain operating mode of the device.

FIG. 1 shows a data processing system including a wearable device and a smart phone according to an example of the present inventive concept. Referring to FIG. 1, a data processing system 100 may include a wearable device 200 and a smart phone 300 which can communicate with each other through a wireless communication network.

Each of the wearable device 200 and the smart phone 300 may be an Internet of Things (IoT) device and hence, may together constitute an IoT. Here, each IoT device may include an accessible interface (for example, a wired interface or a wireless interface). Also, each IoT device may be a device for transmitting or receiving data (wired or wireless data) to or from at least one electronic device (or an IoT device) through the accessible interface.

In this example, the accessible interface may include a local area network (LAN), a wireless local area network (WLAN) such as a wireless fidelity (Wi-Fi), a wireless personal area network (WPAN) such as a Bluetooth, a wireless universal serial bus (USB), a Zigbee, a near field communication (NFC), a radio-frequency identification (RFID), or a mobile cellular network; however, it is not limited thereto. Examples of the mobile cellular network include a $3^{rd}$ generation (3G) mobile cellular network, a $4^{th}$ generation (4G) mobile cellular network, a long term evolution (LTE™) mobile cellular network, and an LTE-Advanced (LTE-A) mobile cellular network, but are not limited thereto.

The wearable device 200 includes a plurality of electrodes 211, 212, 213, and 214. In the example of FIG. 1, two electrodes 211 and 212 are disposed in an upper portion or outer side of a case 201 of the wearable device 200 and two electrodes 213 and 214 are disposed in a lower portion of or inner side the case 201 of the wearable device 200; however, positions of the electrodes 211, 212, 213, and 214 are not limited thereto. The wearable device 200 may also include a display 270 but such a display is optional.

The wearable device 200 also includes a bio-processor 230 embedded in the case 201 of the wearable device 200 as will be described in more detail with reference to FIG. 5, and may include other elements (or components) within the case as will be described with reference to the examples of FIGS. 6, 7, and 8. Thus, the case 201 has the form of a jacket within which electronic components of the device are provided and protected by the case 201. In the illustrated example, the jacket is in the form of a band, e.g., a wrist band or strap that can be secured to the wrist of a user so as to be worn on the wrist. FIG. 1 shows a mechanism including a rivet-like projection at one of the band and to which the other end of the band having a series of holes therein (not shown) can be fixed by popping the rivet-like projection into one of the holes.

The bio-processor 230 may sense or generate a health-related signal (i.e., biological activity or a biological signal) using sensors (for example, the electrodes 211, 212, 213, and 214). The health-related signal may be a bioelectrical impedance analysis (BIA) signal, an electrocardiogram (ECG) signal, or a galvanic skin response (GSR) signal; however, it is not limited thereto.

Figure 2:
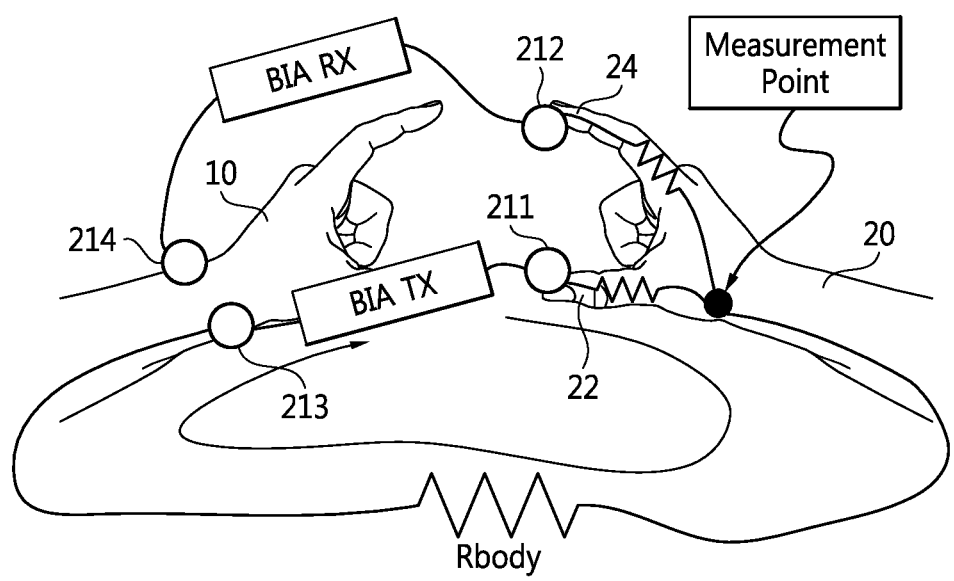
FIG. 2 is a conceptual diagram which illustrates a connection between electrodes for detecting a bioelectrical impedance analysis (BIA) signal using the wearable device shown in FIG. 1.

FIG. 2 is a conceptual diagram which illustrates how a bioelectrical impedance analysis (BIA) signal may be produced using the wearable device shown in FIG. 1. BIA is a widely known method of measuring a body's composition, particularly, body fat. In this example, four electrodes are used for a BIA or for producing a BIA signal. A current source having a frequency of 50 kHz to 1 MHz is required to produce a BIA signal and a bandwidth of the BIA signal may be 50 kHz to 1 MHz; however, it is not limited thereto.

Referring to FIGS. 1 and 2, when a user wears the wearable device 200 on a wrist of his own left (or right) hand 10, and brings a thumb 22 and an index finger 24 of his own right (or left) hand 20 in contact with and presses the electrodes 211 and 212 disposed in the upper portion of the case 201, the electrodes 213 and 214 disposed in the lower portion of the case 201 are held in contact with a skin of the left (or right) hand 10. Current output from each of the electrodes 211 and 213 is supplied to the person's body, a voltage is generated in proportion to a resistance (Rbody) of the body, and the electrodes 212 and 214 may be used to detect the voltage.

Figure 3:
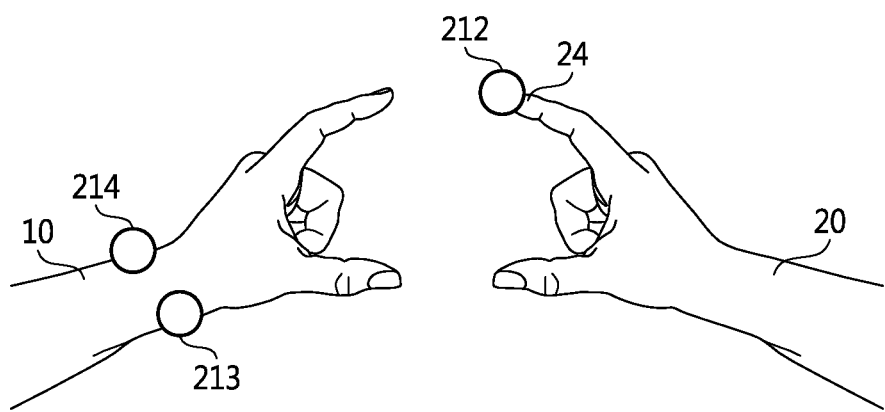
FIG. 3 is a conceptual diagram which illustrates a connection between electrodes for detecting an electrocardiogram (ECG) signal using the wearable device shown in FIG. 1.

FIG. 3 is a conceptual diagram which illustrates how an electrocardiogram (ECG) signal may be produced using the wearable device shown in FIG. 1. An example will be described in which three of the electrodes are used to produce an ECG signal. A current source is not required to produce an ECG signal, and a bandwidth of the ECG signal may be 0.5 Hz to 250 Hz; however, it is not limited thereto.

For example, one of the electrodes 212 is used as positive electrode, another of the electrodes 213 is used as a negative electrode, and still another of the electrodes 214 is used as a reference electrode. The reference electrode 214 may be connected to a battery.

Referring to FIGS. 1 and 3, when a user wears the wearable device 200 on a wrist of his own left (or right) hand 10, and brings an index finger 24 of his own right (or left) hand 20 in contact with and presses the electrode 212, the electrodes 213 and 214 are held in contact with the skin of the left (or right) hand 10. Thus, the electrodes 212 and 213 may be used to detect a minute electrical difference in the skin caused (or induced) by heart muscle depolarizing during each heartbeat.

Figure 4:
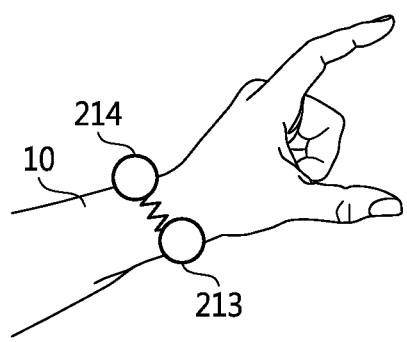
FIG. 4 is a conceptual diagram which illustrates a connection between electrodes for detecting a galvanic skin response (GSR) signal using the wearable device shown in FIG. 1.

FIG. 4 is a conceptual diagram which describes how a galvanic skin response (GSR) signal may be produced using the wearable device shown in FIG. 1. Two electrodes are required to produce a GSR signal. A DC current source is required to produce a GSR signal and a bandwidth of the GSR signal may be 0 Hz to 4 Hz; however, it is not limited thereto.

Referring to FIGS. 1 and 4, when a user wears the wearable device 200 on a wrist of his own left (or right) hand 10 and presses the wearable device 200 using his own right (or left) hand, the electrodes 213 and 214 are held in contact with the skin of the left (or right) hand 10. The electrodes 213 and 214 in contact with the skin may be used to sense or measure electrical resistance (or electrical conductivity) between the electrodes 213 and 214. When current is supplied to one of the electrodes 213 and 214, the electrical resistance is changed according to a reaction of the skin, and accordingly, a voltage may be generated. Therefore, the electrodes 213 and 214 may be used to sense or detect a voltage corresponding to the electrical resistance.

As described referring to FIGS. 2 to 4, when the wearable device 200 includes the plurality of electrodes 211, 212, 213, and 214, a user may use select numbers of the electrodes (for example, four, three, or two electrodes) to obtain different biological signals (for example, BIA signal, ECG signal, or GSR signal) using the wearable device 200. The bio-processor 230 of the wearable device 200 may decide the number of electrodes to be used, in producing a biological signal, based on a selection signal indicating a type of a biological signal to be sensed.

Figure 5:
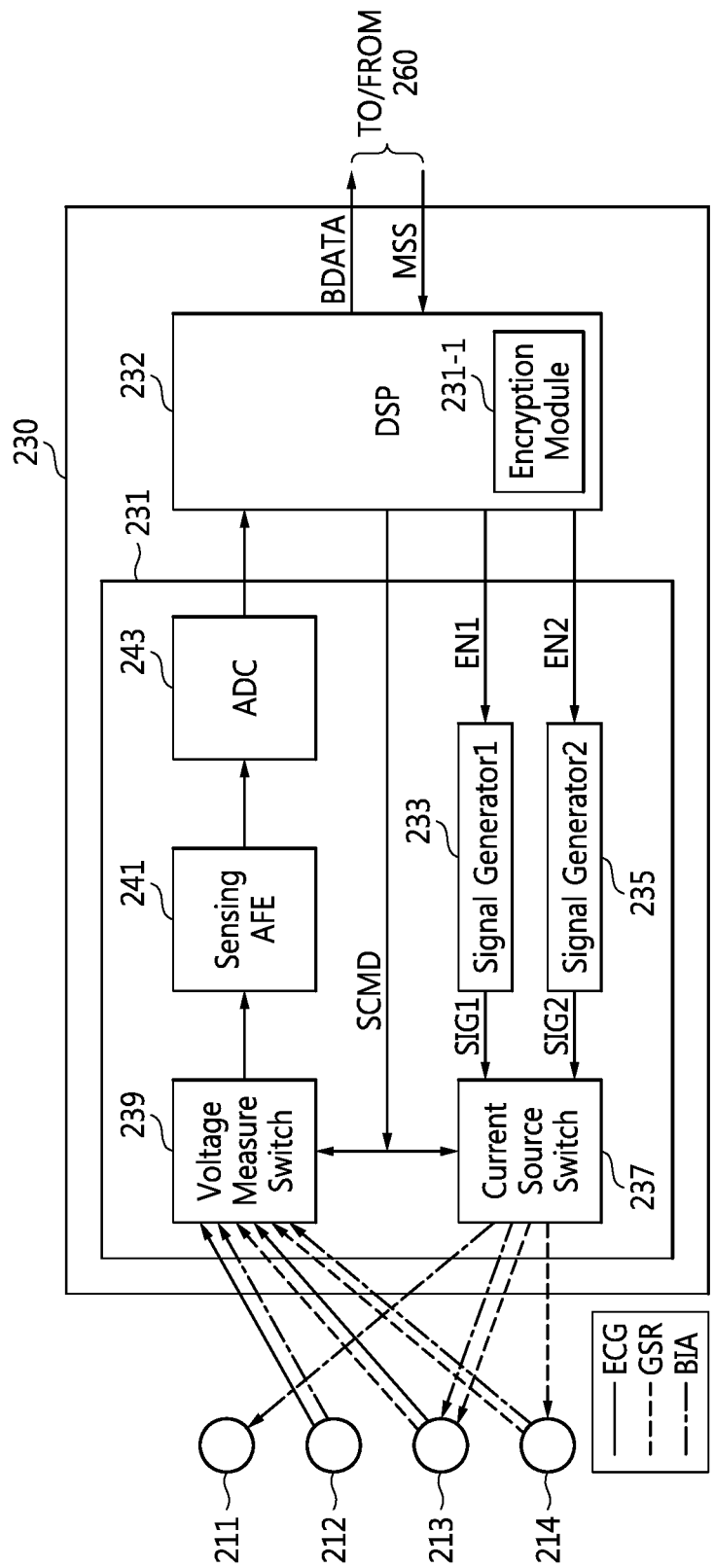
FIG. 5 is a block diagram of a bio-processor shown in FIG. 1 according to an example of the present inventive concept.

FIG. 5 is a block diagram of the bio-processor (i.e., biological processor) shown in FIG. 1 according to an example of the present inventive concept. Referring to FIGS. 1 to 5, the bio-processor 230 may include an electrode control circuit 231 and a digital signal processor (DSP) 232.

The electrode control circuit 231 may decide which ones of the plurality of electrodes 211, 212, 213, and 214 to use as sensing electrodes for sensing a biological signal, under the control of the DSP 232. Moreover, the electrode control circuit 231 may decide which ones of the plurality of electrodes 211 212, 213, and 214 to use as sourcing electrodes for supplying a source current which generates the biological signal, under the control of the DSP 232.

Each of the plurality of electrodes 211, 212, 213, and 214 may be connected to each of a plurality of pads (or a plurality of pins) in the bio-processor 230. Accordingly, the electrode control circuit 231 may decide which ones of the plurality of pads to use as sensing pads for sensing a biological signal, under the control of the DSP 232. Moreover, the electrode control circuit 231 may decide which ones of the plurality of pads to use as sourcing pads for supplying a source current for producing the biological signal, under the control of the DSP 232.

The electrode control circuit 231 may include a first signal generator 233, a second signal generator 235, a current source switch 237, a voltage measuring switch 239, a sensing analog-front end (AFE) 241, and an analog-to-digital converter (ADC) 243. The bio-processor 230 may be embodied as an integrated circuit (IC) or a system-in package (SiP); however, it is not limited thereto.

Figure 6:
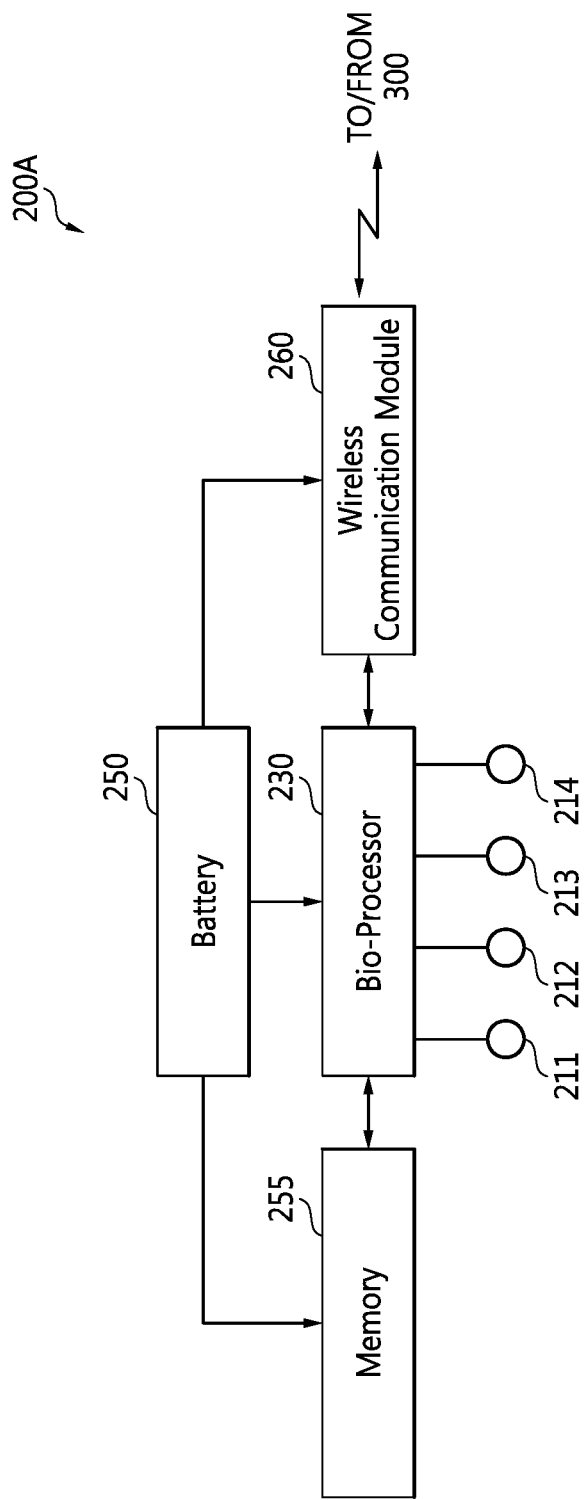
FIG. 6 is a block diagram of a wearable device according to examples of the present inventive concept, which includes the bio-processor shown in FIG. 5.
Figure 7:
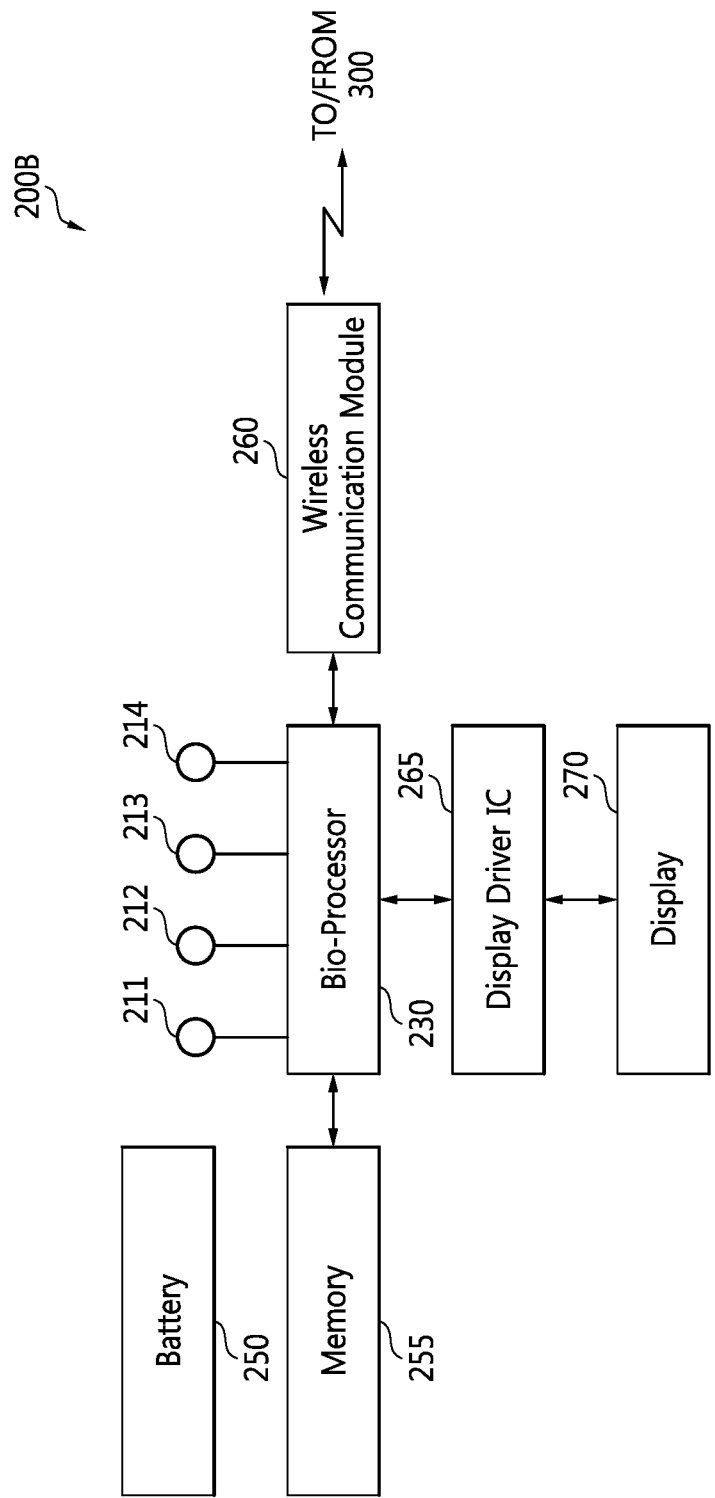
FIG. 7 is a block diagram of the wearable device according to examples of the present inventive concept, which includes the bio-processor shown in FIG. 5.
Figure 8:
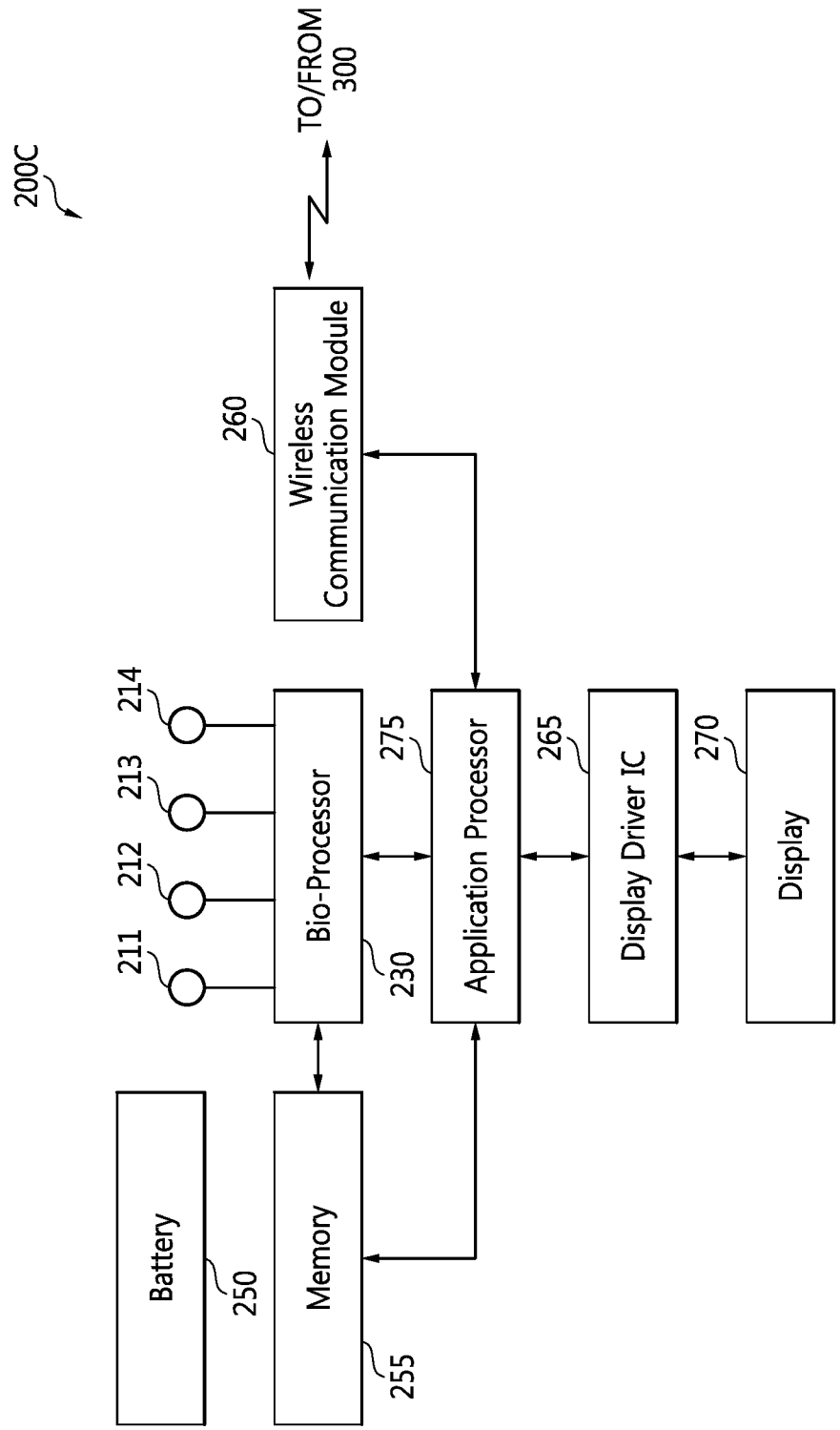
FIG. 8 is a block diagram of the wearable device according to examples of the present inventive concept, which includes the bio-processor shown in FIG. 5.

The DSP 232 may receive and process a digital signal output from the ADC 243 and transmit a processed digital signal (for example, biological data BDATA) to a wireless communication module 260 examples of which are shown in FIGS. 6, 7 and 8. The DSP 232 may control an operation of each of components 233, 235, 237, and 239 in response to a selection signal MSS transmitted from the wireless communication module 260. The DSP 232 may serve as a controller. For example, the DSP 232 may generate a first enable signal EN1, a second enable signal EN2, and a switch enable signal SCMD in response to a selection signal MSS.

The first signal generator 233 may be enabled or disabled in response to the first enable signal EN1. For example, the first signal generator 233 may generate a first signal SIG1 for sensing a BIA signal. The first signal SIG1 may be a sinusoidal wave signal as a current signal; however, it is not limited thereto. The first signal generator 233 may serve as a first current source.

The second signal generator 235 may be enabled or disabled in response to the second enable signal EN2. For example, the second signal generator 235 may generate a second signal SIG2 for measuring a GSR signal. The second signal SIG2 may be a pulse signal as a current signal; however, it is not limited thereto. The second signal generator 235 may serve as a second current source. One of the signal generators 233 and 235 may be enabled or all of the signal generators 233 and 235 may be disabled. Each of the current source switch 237 and the voltage measuring switch 239 may be enabled or disabled in response to a switch enable signal SCMD.

The current source switch 237 enabled may transmit the first signal SIG1 or the second signal SIG2 to select ones of the electrodes 211, 212, 213, and 214, thereby designating those electrodes as sourcing electrodes. The current source switch 237 may select the sourcing electrodes from among the plurality of electrodes 211, 212, 213, and 214 in response to a switch enable signal SCMD.

For example, when the selection signal MSS indicates a sensing of a BIA signal, the DSP 232 may generate an activated first enable signal EN1 and a deactivated second enable signal EN2, and generate a switch control signal SCMD having a first value. Accordingly, the first signal generator 233 may generate a first signal SIG1 in response to the activated first enable signal EN1.

Referring to FIG. 2, the current source switch 237 may select the electrodes 211 and 213 among the plurality of electrodes 211, 212, 213, and 214 as the sourcing electrodes in response to the switch control signal SCMD having a first value, and transmit the first signal SIG1 to the sourcing electrodes 211 and 213 as a source current.

The voltage measuring switch 239 may select the electrodes 212 and 214 among the plurality of electrodes 211, 212, 213, and 214 as sensing electrodes in response to the switch control signal SCMD having a first value, and sense a biological signal (that is, BIA signal) caused by the source current through the sensing electrodes 212 and 214. The sensing AFE 241 may amplify a difference between voltages (for example, BIA signals) output from the sensing electrodes 212 and 214, remove noise from the amplified signal, and transmit the resulting noise-filtered analog signal to the ADC 243.

For example, when the selection signal MSS indicates an ECG signal is to be produced, the DSP 232 may generate a deactivated first enable signal EN1 and a deactivated second enable signal EN2, and generate a switch control signal SCMD having a second value. Accordingly, each of the signal generators 233 and 235 is deactivated. The current source switch 237 is disabled in response to the switch control signal SCMD having a second value. That is, each of the signal generators 233 and 235 may be disconnected from the plurality of electrodes 211, 212, 213, and 214.

Referring to FIG. 3, the voltage measuring switch 239 may select the electrodes 212 and 213 among the plurality of electrodes 211, 212, 213, and 214 as sensing electrodes in response to the switch control signal SCMD having a second value, and sense a biological signal (corresponding to an ECG signal) caused by the current through the sensing electrodes 212 and 213. Accordingly, the sensing AFE 241 may amplify a potential difference between the electrodes 212 and 213 and output the same as an amplified signal, remove noise from the amplified signal, and transmit the resulting noise-filtered analog signal to the ADC 243.

For example, when the selection signal MSS indicates that a GSR signal is to be produced, the DSP 232 may generate a deactivated first enable signal EN1 and an activated second enable signal EN2, and generate a switch control signal SCMD having a third value. Accordingly, the second signal generator 235 may generate a second signal SIG2 in response to the activated second enable signal EN2.

Referring to FIG. 4, the current source switch 237 may select the electrodes 213 and 214 among the plurality of electrodes 211, 212, 213, and 214 as sourcing electrodes in response to the switch control signal SCMD having a third value, and transmit a second signal SIG2 to the sourcing electrodes 213 and 214 as a source current.

The voltage measuring switch 239 may select the electrodes 213 and 214 among the plurality of electrodes 211, 212, 213, and 214 as sensing electrodes in response to the switch control signal SCMD having a third value, and sense a biological signal (corresponding to a GSR signal) caused by the source current through the sensing electrodes 213 and 214. Accordingly, the sensing AFE 241 may amplify a potential difference between the electrodes 213 and 214, remove a noise from the amplified signal, and transmit the resulting noise-filtered analog signal to the ADC 243.

The ADC 243 may convert an analog signal processed by the sensing AFE 241 into a digital signal and transmit the digital signal to the DSP 231. The digital signal may be data related to BIA, data related to ECG, or data related to GSR.

The sensing AFE 241 and the ADC 243 may configure an AFE. The AFE may amplify an output signal of the voltage measuring switch 239, convert an amplified signal into a digital signal, and transmit the digital signal to the DSP 232.

The DSP 232 may process the digital signal and transmit biological data BDATA corresponding to a result of the processing to the wireless communication module (or wireless transceiver) 260 shown in FIG. 6, 7, or 8. The biological data BDATA may be biological data encrypted by an encryption module 231-1 embedded in the DSP 232.

As described above, the bio-processor 230 may decide which ones of the plurality of electrodes 211, 212, 213, and 214 to use as sensing electrodes and which ones of the plurality of electrodes 211, 212, 213, and 214 to use as sourcing electrodes based on the selection signal MSS indicating a type of a biological information to be sensed and corresponding biological signal to be produced.

FIG. 6 is a block diagram of a wearable device according to examples of the present inventive concept, which includes the bio-processor shown in FIG. 5. Referring to FIGS. 1 to 6, a wearable device 200A may include the bio-processor 230 connected to the plurality of electrodes 211, 212, 213, and 214, a battery 250, a memory 255, and the wireless communication module 260.

The battery 250 may supply operation voltages to each of the bio-processor 230, the memory 255, and the wireless communication module 260, respectively. The bio-processor 230 may store biological data BDATA or more specifically, encrypted biological data BDATA, generated by the DSP 232 in the memory 255 or transmit the biological data BDATA to a smart phone 300 through the wireless communication module 260. The memory 255 may be embodied as a volatile memory or a non-volatile memory. The wireless communication module 260 may communicate with the smart phone 300 through a WLAN such as Wi-Fi, a WPAN such as Bluetooth, a wireless USB, a Zigbee, an NFC, an RFID, or a mobile cellular network.

FIG. 7 is a block diagram of a wearable device according to examples of the present inventive concept, which includes the bio-processor shown in FIG. 5. Referring to FIGS. 1 to 5 and 7, a wearable device 200B may include the bio-processor 230 connected to the plurality of electrodes 211, 212, 213, and 214, a battery 250, a memory 255, the wireless communication module 260, a display driver IC 265, and a display 270.

The battery 250 may supply operation voltages to each of the components 230, 255, 260, 265, and 270, respectively. The bio-processor 230 may transmit biological data BDATA to the display driver IC 265. The display driver IC 265 may display the biological data BDATA on the display 270. Examples of the biological data BDATA displayed on the display 270 will be described later with reference to FIGS. 10, 11, and 12.

FIG. 8 is a block diagram of a wearable device according to examples of the present inventive concept, which includes the bio-processor shown in FIG. 5. Referring to FIGS. 1 to 5 and 8, a wearable device 200C may include the bio-processor 230 connected to the plurality of electrodes 211, 212, 213, and 214, a battery 250, a memory 255, the wireless communication module 260, a display driver IC 265, a display 270, and an application processor 275.

The battery 250 may supply operation voltages to the components 230, 255, 260, 265, 270, and 275. The application processor 275 may control an operation of each of the components 230, 250, 255, 260, 265, and 270.

The bio-processor 230 may transmit biological data BDATA to the application processor 275. The application processor 275 may transmit the biological data BADATA to the display driver IC 265. The display drier IC 265 may display the biological data BDATA on the display 270. Again, examples of the biological data BDATA displayed on the display 270 are shown in and will be described with reference to FIGS. 10, 11, and 12.

According to examples, the biological data BDATA may be transmitted to the smart phone 300 under the control of the bio-processor 230 or the application processor 275. The wearable devices 200A, 200B, and 200C are examples of the configuration of the wearable device 200 of FIG. 1.

Figure 9:
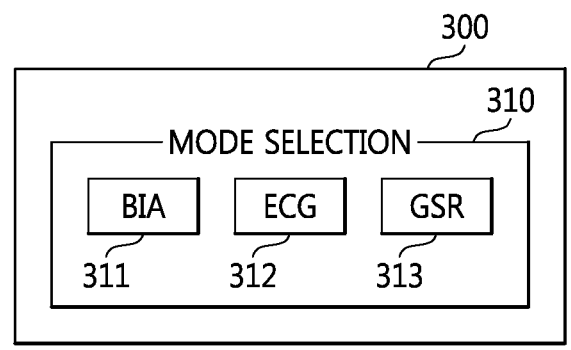
FIG. 9 is a schematic diagram of a graphic user interface which is provided by an application for selecting an operation mode of the bio-processor shown in FIG. 5.

FIG. 9 shows a graphic user interface which is provided by an application for selecting an operation mode of the bio-processor shown in FIG. 5. Referring to FIGS. 1 and 6 to 9, an application program (app or software) executed by the smart phone 300 may provide a user with a graphic user interface (GUI) 310. The user may select a type of a biological signal to be sensed through the GUI 310. The user may select a first GUI 311 for sensing a BIA signal, a second GUI 312 for sensing an ECG signal, or a third GUI 313 for sensing a GSR signal. An application program executed by the smart phone 300 may generate a selection signal MSS indicating a type of a biological signal to be sensed, and transmit the selection signal MSS to the wireless communication module 260 of the wearable device 200. The wireless communication module (or wireless transmitter) 260 may transmit the selection signal MSS to the bio-processor 230.

Even if an application program executed by the smart phone 300 is shown in FIG. 9, an application program executed by a CPU of the bio-processor 230 of the wearable device 200B of FIG. 7 may provide a user with a GUI that is the same as or similar to the GUI 310 of FIG. 9 through the display 270.

In addition, an application program executed by a CPU of the application processor 275 of the wearable device 200C of FIG. 8 may provide a user with a GUI that is the same as or similar to the GUI 310 of in FIG. 9 through the display 270. At this time, the bio-processor 230 or a CPU of the application processor 275 may generate a selection signal MSS for indicating a type of a biological signal to be sensed and transmit the selection signal MSS to the DSP 232.

Figure 10:
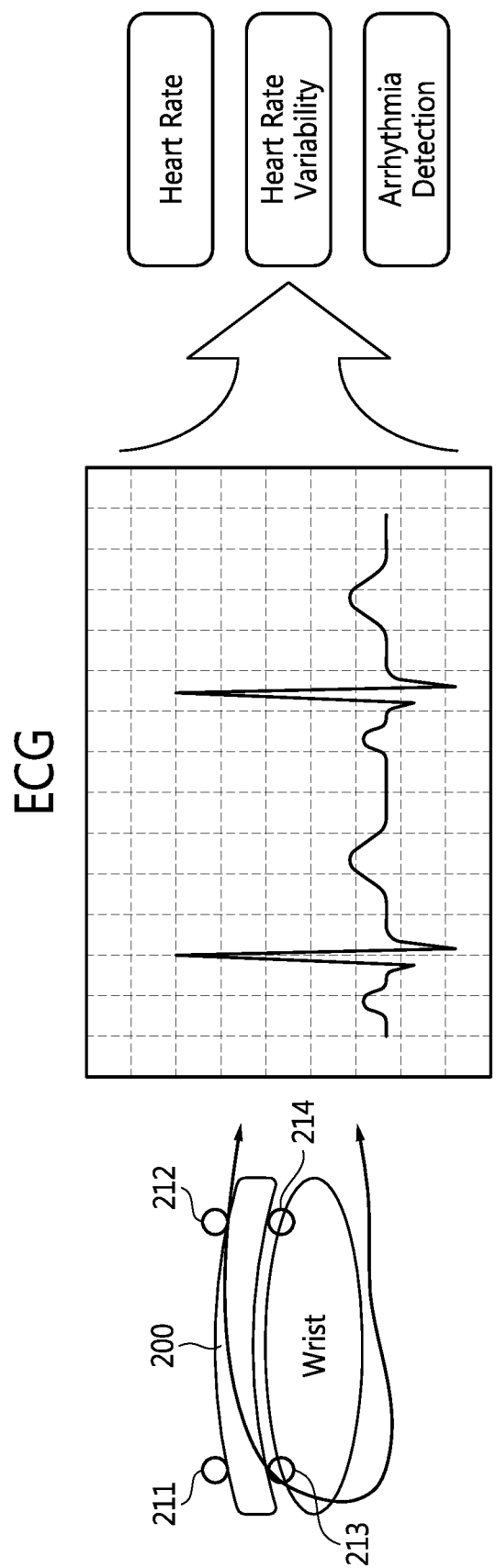
FIG. 10 shows an ECG waveform provided by and conditions which can be detected using the wearable device shown in FIG. 1.

FIG. 10 shows an ECG waveform and conditions that can be sensed by the wearable device shown in FIG. 1. Referring to FIGS. 1, 3, and 10, an ECG signal generated through the sensing electrodes 212 and 213 may be displayed on the display 270 or smart phone 300.

A biological signal analysis application program executed by a CPU of the bio-processor 230, a CPU of the application processor 275, or a CPU of the smart phone 300 may detect a heart rate, heart rate variability, and arrhythmia by processing the ECG signal, and display a result of the detection on the display 270 or the display of the smart phone 300.

Figure 11:
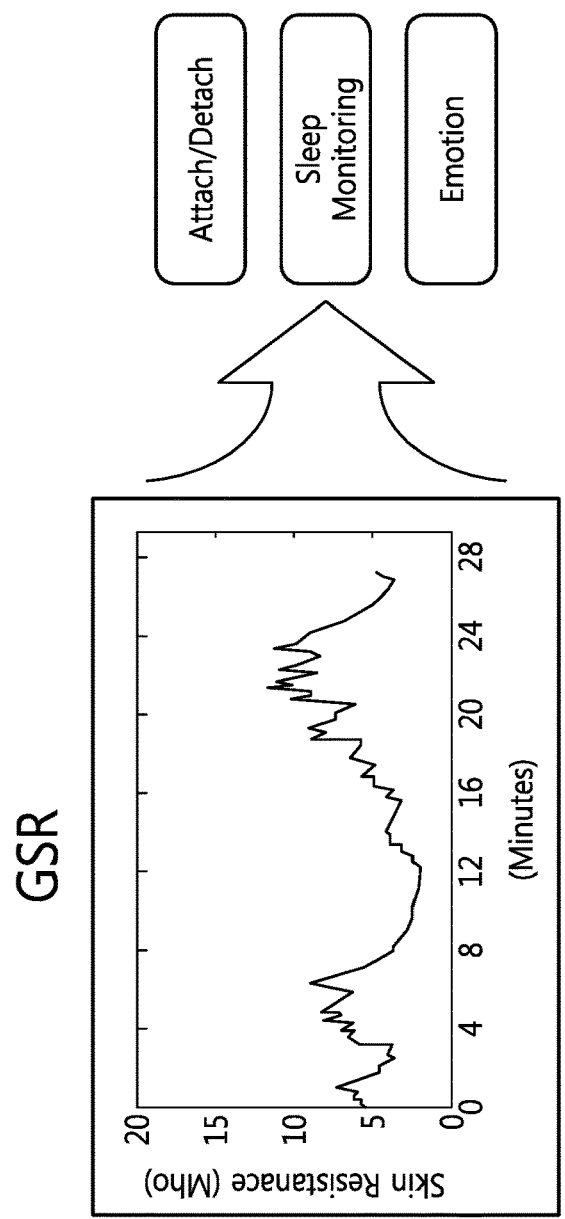
FIG. 11 shows a GSR waveform provided by and conditions that can be detected using the wearable device shown in FIG. 1.

FIG. 11 shows a GSR waveform and conditions sensed by the wearable device shown in FIG. 1. Referring to FIGS. 1, 4, and 11, a GSR signal produced through the sensing electrodes 213 and 214 may be displayed on the display 270 or smart pone 300.

The biological signal analysis application program executed by the CPU of the bio-processor 230, the CPU of the application processor 275, or the CPU of the smart phone 300 may determine whether the user is wearing the wearable device 200 on his or her wrist, may determine whether the user is sleeping, or may determine an emotional state of the user, and display a result of the determination on the display 270 or smart phone 300.

Figure 12:
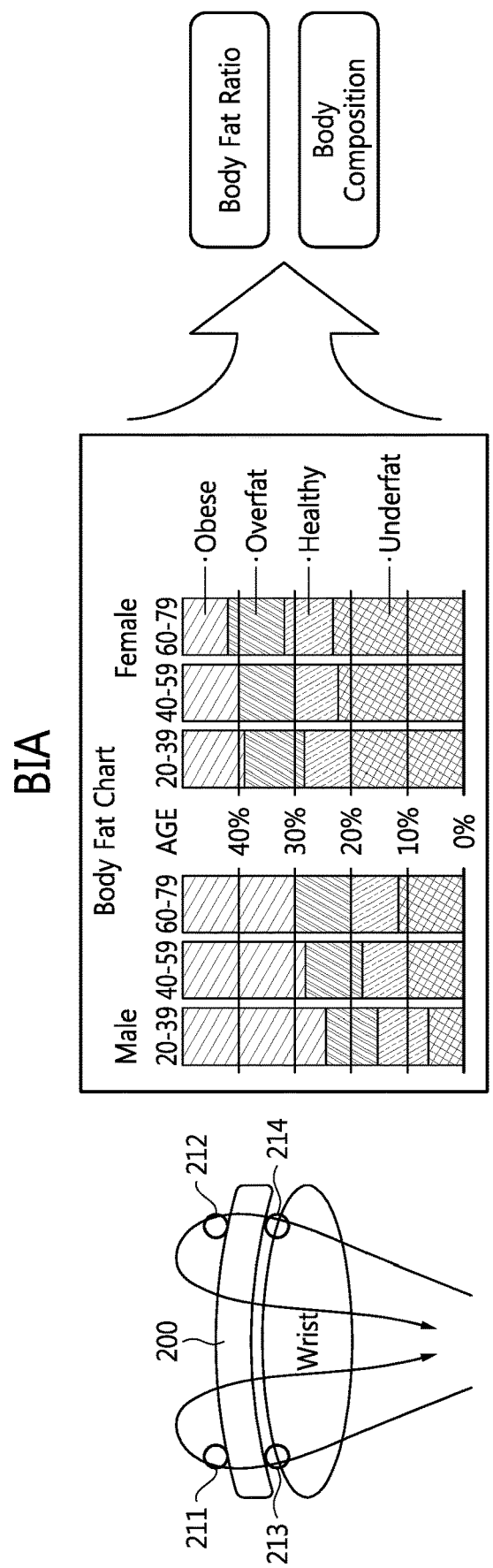
FIG. 12 shows a BIA waveform provided by and conditions that can be detected using the wearable device shown in FIG. 1.

FIG. 12 shows a BIA waveform and conditions sensed by the wearable device shown in FIG. 1. Referring to FIGS. 1, 2, and 12, a BIA signal produced through the sensing electrodes 212 and 214 may be displayed on the display 270 or smart phone 300.

The biological signal analysis application program executed by the CPU of the bio-processor 230, the CPU of the application processor 275, or the CPU of the smart phone 300 may determine a body fat ratio and a body composition using a BIA signal processed by the bio-processor 230, and display a result of the determination on the display 270 or smart phone 300.

Figure 13:
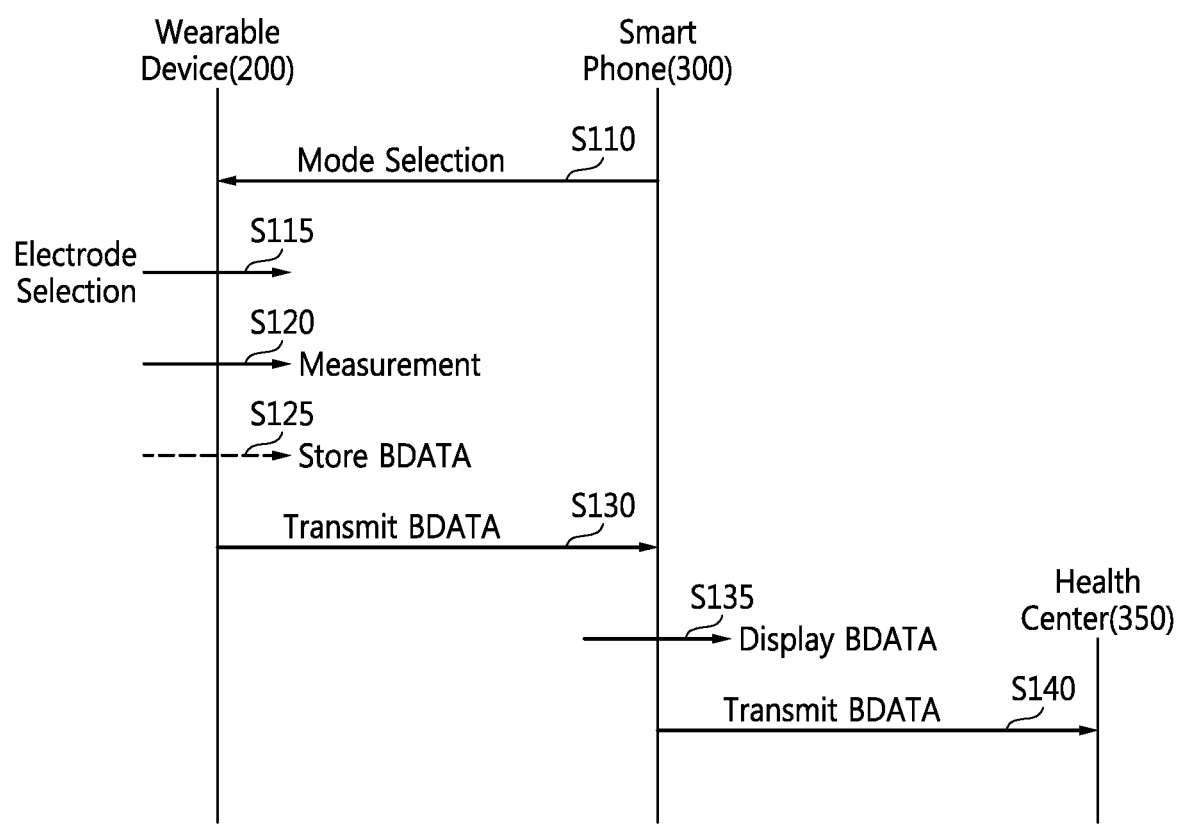
FIG. 13 is a data flow diagram of an operation of the data processing system shown in FIG. 1.

FIG. 13 shows a data flow in an operation of the data processing system shown in FIG. 1. Referring to FIGS. 1 to 13, when a user selects a type (or a mode selection) of a biological signal to be sensed using the GUI 310 shown in FIG. 9, an application program executed by the smart phone 300 may transmit a selection signal MSS for indicating a type (or a mode selection) of a biological signal to be sensed through its wireless communication module to the wireless communication module 260 of the wearable device 200 (S110).

The bio-processor 230 may decide which ones of the plurality of electrodes 211, 212, 213, and 214 to use as sensing electrodes for sensing a biological signal and/or which ones of the plurality of electrodes 211, 212, 213, and 214 to use as sourcing electrodes for supplying a source current which causes the biological signal under the control of the DSP 232 operating in response to a selection signal MSS (S115).

The bio-processor 230 may receive a biological signal from the sensing electrodes selected by the bio-processor 230 (S120), process (for example, amplification, noise removal, and analog-to-digital conversion) the signal, generate biological data BDATA from the processed signal, and store the biological data BDATA in the memory 255 (S125). In some cases, though, the biological data BDATA may not be stored in the memory 255.

The biological data BDATA generated by the bio-processor 230 may be transmitted to the smart phone 300 through the wireless communication module 260 (S130). An application program executed by the smart phone 300 may display biological data (for example, BIA data, ECG data, or GSR data) as described with reference to FIG. 10, 11, or 12 on (the display of) the smart phone 300 (S135).

According to examples, the application program executed by the smart phone 300 may transmit the biological data (for example, BIA data, ECG data, or GSR data) to a server, for example, a server of a health center 350 (S140). The server of the health center 350 may analyze the biological data (for example, BIA data, ECG data, or GSR data) and transmit a result of the analysis to the smart phone 300.

Figure 14:
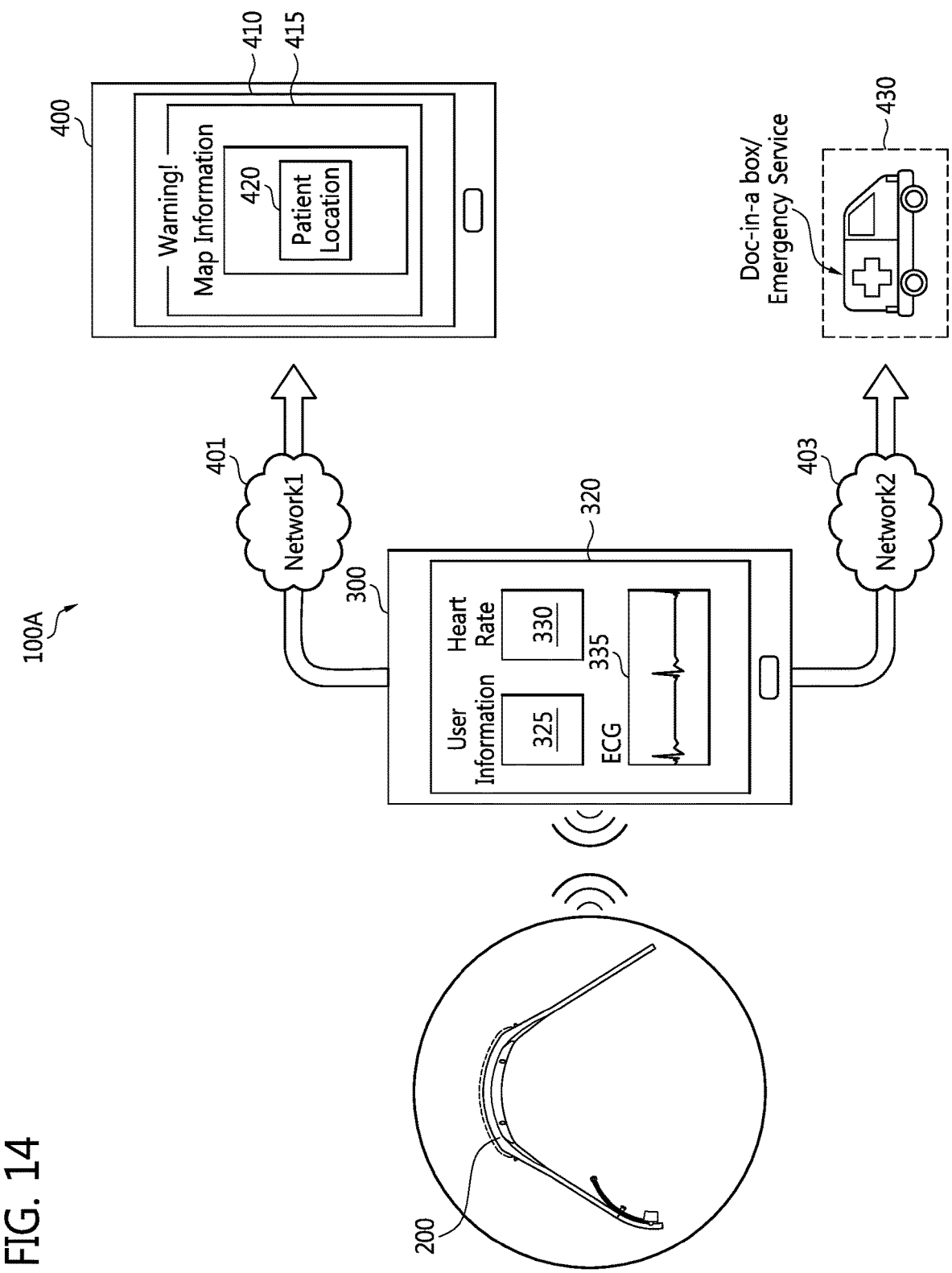
FIG. 14 is a block diagram of the data processing system including the wearable device shown in FIG. 1.

FIG. 14 is a block diagram of another example of a data processing system including the wearable device shown in FIG. 1. Referring to FIGS. 1 to 14, a data processing system 100A may include the wearable device 200, a first smart device 300, a second smart device 400, and an emergency medical system 430.

When a wireless communication module of the first smart device 300 transmits a biological data transmission request to the wearable device 200 in a wireless manner, the wireless communication module 260 of the wearable device 200 may transmit the data transmission request to the bio-processor 230 or the application processor 275.

The bio-processor 230 or the application processor 275 may read biological data from the memory 255 in response to the data transmission request and transmit read biological data to a wireless communication module of the first smart device 300 through the wireless communication module 260. A first application (or app) executed by a CPU of the first smart device 300 may display at least one of user information 325, a heart rate 330, and an ECG signal 335 of a user wearing the wearable device 200 on a display 320 based on the biological data. The ECG signal 335 shown in FIG. 14 is exemplary only; the first application (or app) may display at least one of a BIA signal, an ECG signal, and a GSR signal on the display 320.

The wireless communication module of the first smart device 300 may transmit warning data to the second smart device 400 through a network 401 under the control of the first application executed by the CPU of the first smart device 300.

For example, the first application may analyze biological data transmitted from the wearable device 200. When an abnormality is detected in a heart of a user wearing the wearable device 200 according to a result of the analysis, the first smart device 300 may generate warning data under the control of the first application and transmit the warning data to the second smart device 410.

For example, the first application may transmit positional information of the user output from a GPS receiver of the wearable device 200 or positional information of the first smart device 300 output from a GPS receiver of the first smart device 300 to a wireless communication module of the first smart device 300 along with the warning data. Accordingly, the wireless communication module of the first smart device 300 may transmit the warning data and the positional information to the second smart device 400.

A second application (or app) executed by a CPU of the second smart device 400 may display a warning message 415 including map information on a display 410 of the second smart device 400. The map information may include a map 420 representing a position of the user. According to an example, the map 420 may be generated by a second application, and may be received from the first smart device 300 along with the positional data or the warning data.

The wireless communication module of the first smart device 300 may transmit a signal for help to the emergency medical system 430 through a network 403 under the control of a first application executed by a CPU of the first smart device 300.

The wireless communication module 260 of the wearable device 200 may transmit biological data or an analysis result of the biological data to the first smart device 300. The first smart device 300 may transmit warning data to the second smart device 400 through the network 401 or transmit a signal for help to the emergency medical system 430 through the network 403 based on the biological data or the analysis result. The emergency medical system 430 may be a computer of any type of (e.g., physically located in) an emergency center, a fire station, or a hospital.

Figure 15:
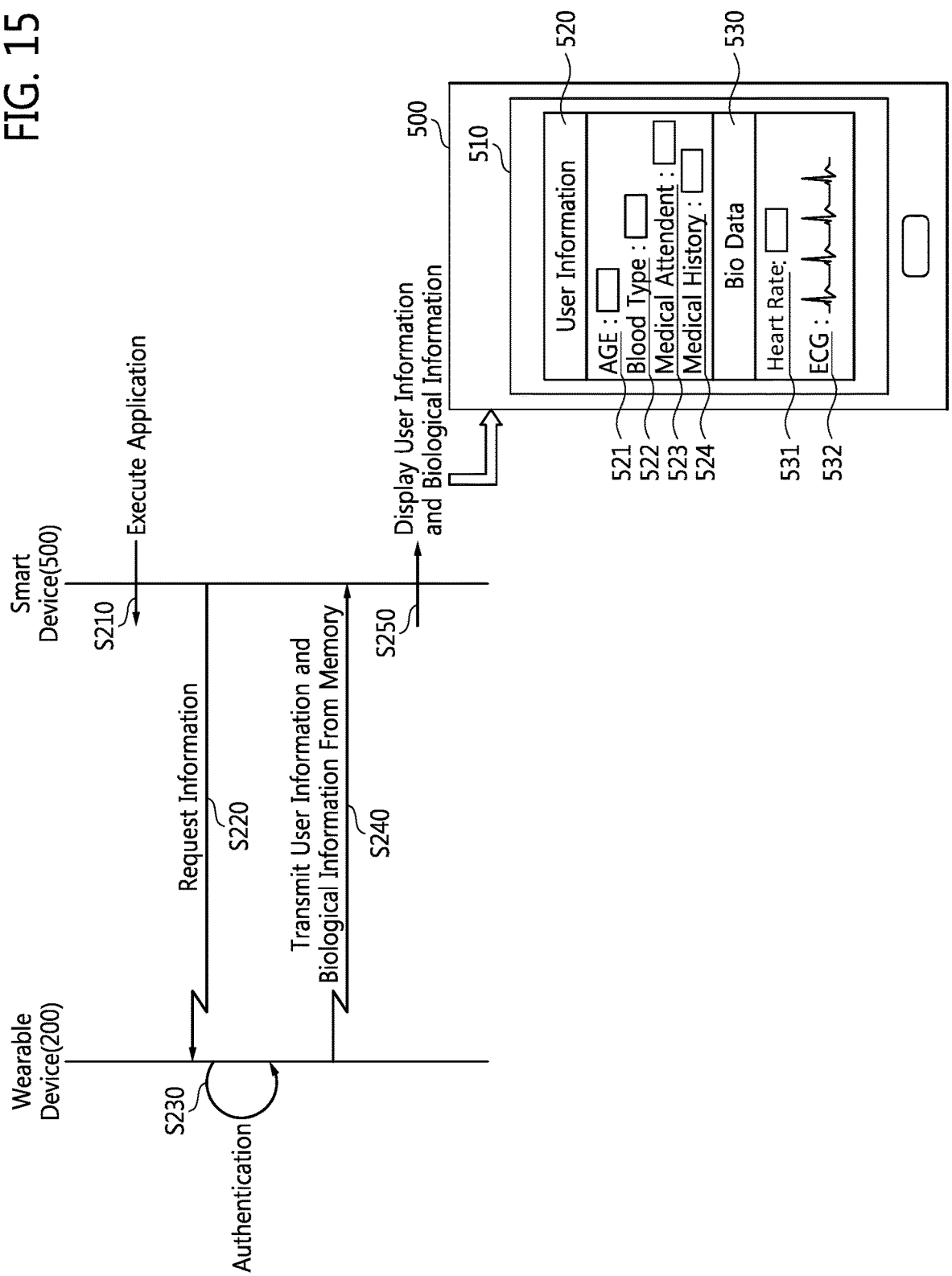
FIG. 15 is a block diagram of the data processing system including the wearable device show in FIG. 1.

FIG. 15 is a block diagram of another example of a data processing system including the wearable device show in FIG. 1. Referring to FIGS. 1 to 12, and 15, a user of a smart device 500 may execute an application (or app) APP installed in the smart device 500 (S210).

A wireless communication module of the smart device 500 may transmit an information request to the wearable device 200 according to the application APP executed by the CPU of the smart device 500 (S220).

The bio-processor 230 or the application processor 275 of the wearable device 200 may perform an authentication for the information request input through the wireless communication module 260 (S230).

After authentication for the information request is completed, the bio-processor 230 or the application processor 275 may read user information and biological data from the memory 255, encrypt the user information and the biological data through an encryption module, and transmit encrypted user information and encrypted biological data to the wireless communication module 260. The wireless communication module 260 may transmit the encrypted user information and the encrypted biological data to the smart device 500 (S240).

The application APP executed by the smart device 500 may decrypt each of the encrypted user information and the encrypted biological data, and display decrypted user information 520 and decrypted biological data 530 on the display 510 of the smart device 500 (S250). The decrypted user information 520 may include an age 521, a blood type 522, a medical attendant 523, and a medical history 524; however, it is not limited thereto. The decrypted biological data 530 may include a heart rate 531 and an ECG signal 532, for example. Although the ECG signal 532 is shown as an example of the biological data 530 in FIG. 15, the biological data may include a BIA signal or a GSR signal according to some examples.

The application APP executed by the smart device 500 may detect, predict, or analyze sudden cardiac arrest (SCA) of a user wearing the wearable device 200 using the ECG signal. For example, the application APP may detect, predict, or analyze ventricular fibrillation of the user using the ECG signal and/or cardiac arrhythmia of the user using ventricular Tachycardia of the user.

A health care professional (for example, a medical team or an emergency medical technician) in possession of the smart device 500 may determine a state of health of the person wearing the wearable device 200 using the user information 520 and the biological data 530, and perform an appropriate medical treatment or an emergency measure on the person according to a result of the determination.

Figure 16:
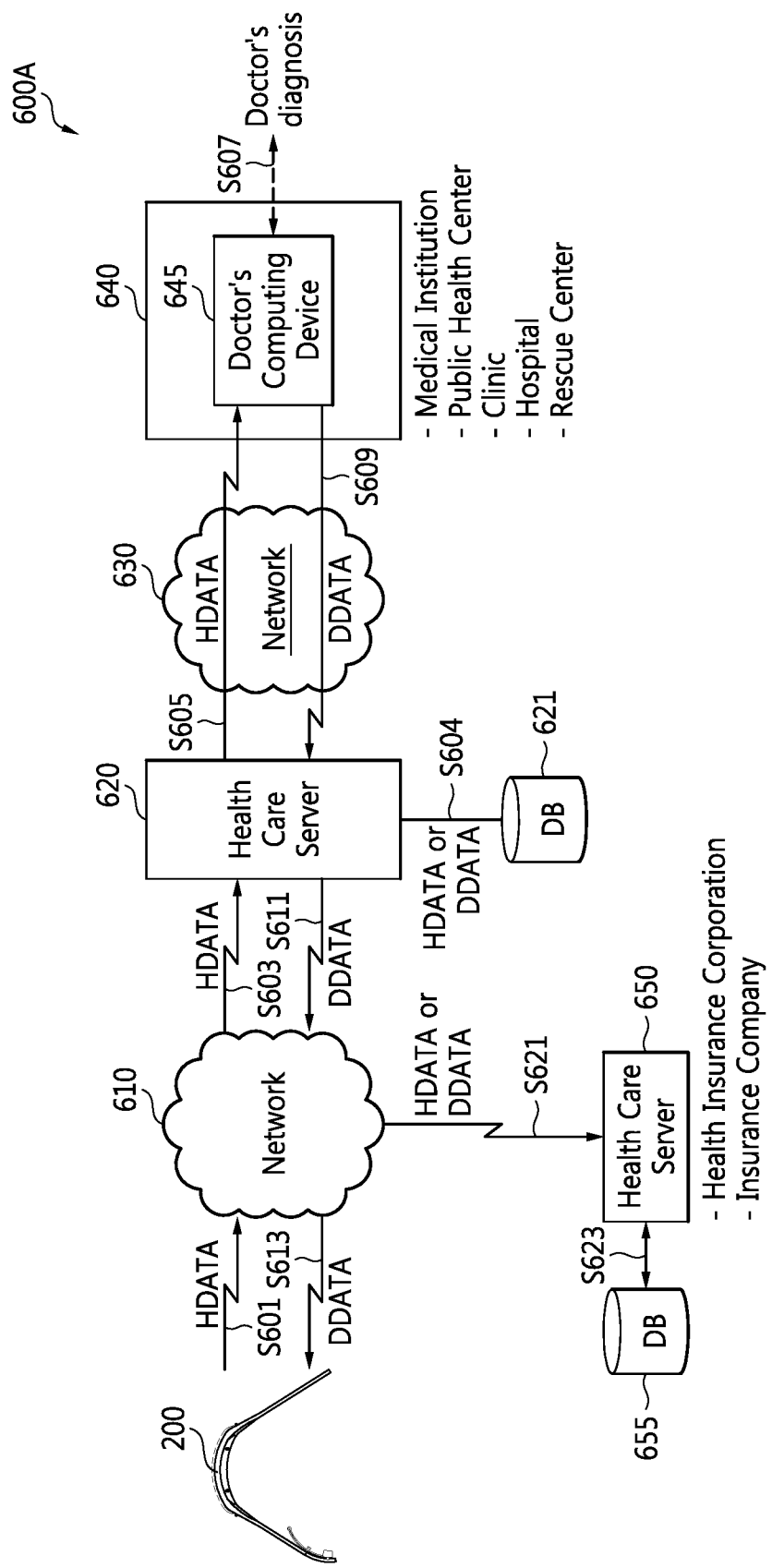
FIG. 16 is a block diagram of a health care system including the wearable device shown in FIG. 1.

FIG. 16 is a block diagram of another example of a data processing system including the wearable device shown in FIG. 1. Referring to FIGS. 1 to 12, and 16, a data processing system 600A may be used to provide a telemedicine service. The data processing system 600A may include the wearable device 200, a wireless network 610, and a first medical server 620 for communicating with the wearable device 200 through the wireless network 610.

According to examples, the data processing system 600A may further include a second medical server 650 for communicating with the wearable device 200 and/or the first medical server 620 through the wireless network 610. For example, a health insurance corporation and/or an insurance company may manage the second medical server 650 and a database 655.

The wireless communication module 260 of the wearable device 200 may transmit data HDATA corresponding to biological data (for example, data related to a BIA signal, data related to an ECG signal, and/or data related to a GSR signal) to the first medical server 620 (S601) or the second medical server 650 (S621) through the network 610 under the control of an application executed by the bio-processor 230 or the application processor 275.

The application may store a uniform resource locator (URL) of the first medical server 620 and/or a URL of the second medical server 650. Accordingly, the wireless communication module 260 of the wearable device 200 may transmit data HDATA to each of the servers 620 and 650 corresponding to each URL under the control of the application.

The data HDATA may include biological data, data generated based on the biological data, and user information of the wearable device 200. For example, data generated based on the biological data may include data for ventricular fibrillation, data for ventricular tachycardia, a heart rate, or cardiac arrhythmias; however, it is not limited thereto.

The wireless network 610 may transmit the data HDATA to the first medical server 620 and/or the second medical server 650 (S603 and/or S621). The first medical server 620 may store the data HDATA in the database 621 (S604), and transmit the data HDATA to a computing device 645 of a doctor through the network 630 (S605). For example, the computing device 645 of a doctor may be a PC or a tablet PC; however, it is not limited thereto. The doctor may work at a medical institution, a public health care center, a clinic, a hospital, or a rescue center.

The doctor may diagnose a state of health of a user wearing the wearable device 200 using the data HDATA displayed through the computing device 645 and input diagnosis data in the computing device 645 (S607). The computing device 645 may transmit the diagnosis data DDATA to the first medical server 620 through the network 630 (S609), and the first medical server 620 may store the diagnosis data DDATA in the database 621 (S604) and transmit the diagnosis data DDATA to the network 610 (S611). The network 610 may transmit the diagnosis data DDATA to the wearable device 200 (S613) or to the second medical server 650 (S621). The wearable device 200 may store the diagnosis data DDATA in the memory 255 or output the diagnosis data DDATA through the display device 270. The second medical server 650 may store the diagnosis data DDATA in the database 655 (S623).

The servers 620 and 650 may store the data HDATA and DDATA in the databases 621 and 655 or analyze the data HDATA and DDATA. Moreover, each of the servers 620 and 650 may transmit a result of the analysis to each of the networks 610 and 630.

Figure 17:
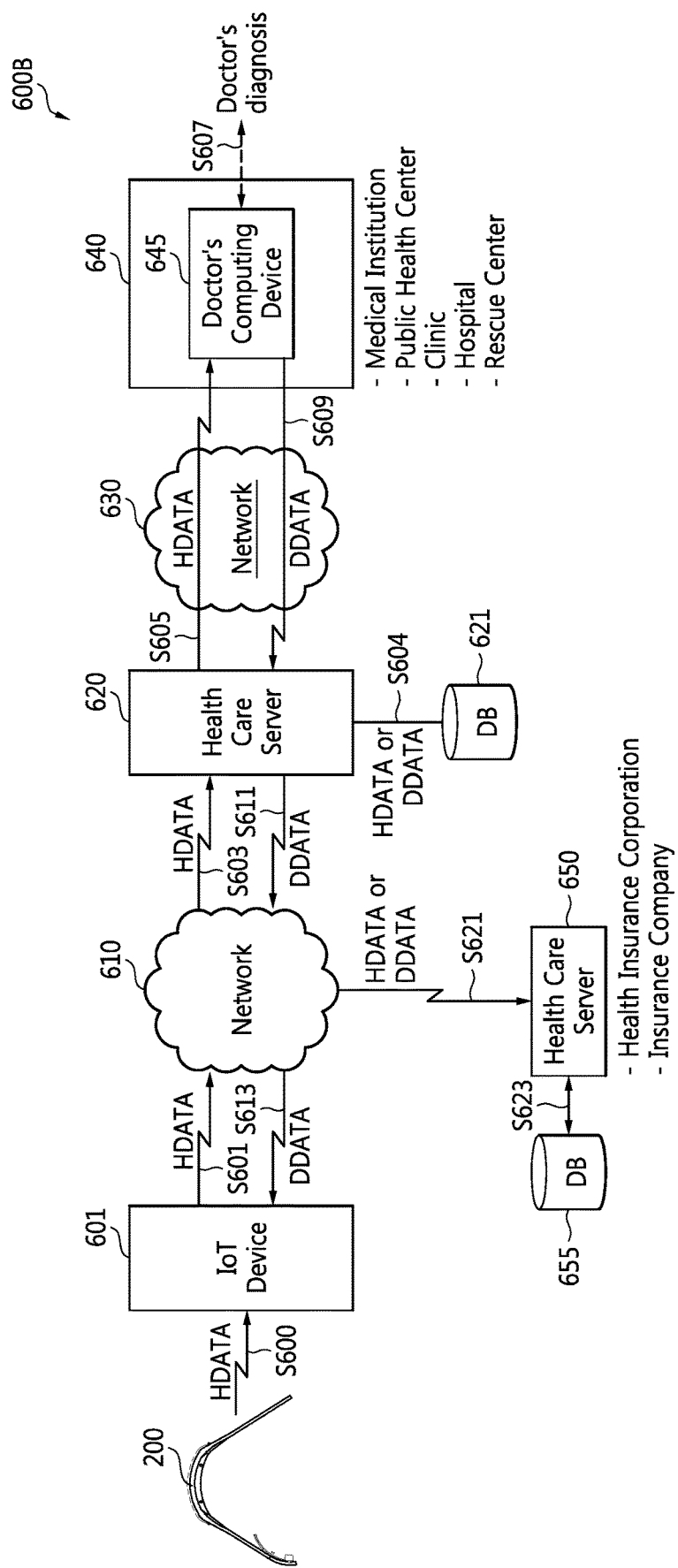
FIG. 17 is a block diagram of the health care system including the wearable device shown in FIG. 1.

FIG. 17 is a block diagram of another example of a data processing system including the wearable device shown in FIG. 1. Referring to FIGS. 1 to 12, and 17, a data processing system 600B may include the wearable device 200, an IoT device 601, and the first medical server 620 for communicating with the IoT device 601 through the wireless network 610.

The data processing system 600B of FIG. 17 is similar to the data processing system 600A of FIG. 16 in terms of structure and operation except that the wearable device 200 transmits or receives data to or from the wireless network 610 through the IoT device 601. The IoT device 601 may be the smart phone 300 of FIG. 1; however, it is not limited thereto.

That is, the wearable device 200 may transmit data HDATA generated by the wearable device 200 to the IoT device 601 (S600). The wearable device 200 may automatically transmit the data HDATA to the IoT device 601 according to a request of the IoT device 601 or when an abnormality is detected in a heart of a user wearing the wearable device 200 (S600).

The IoT device 601 may transmit the data HDATA to the network 610 (S601) and receive the diagnosis data DDATA output from the network 610 (S613). The IoT device 601 may display the diagnosis data DDATA on a display of the IoT device 601. Accordingly, a user of the IoT device 601 may perform an appropriate medical care or first aid on a user of the wearable device 200 using the diagnosis data DDATA.

Figure 18:
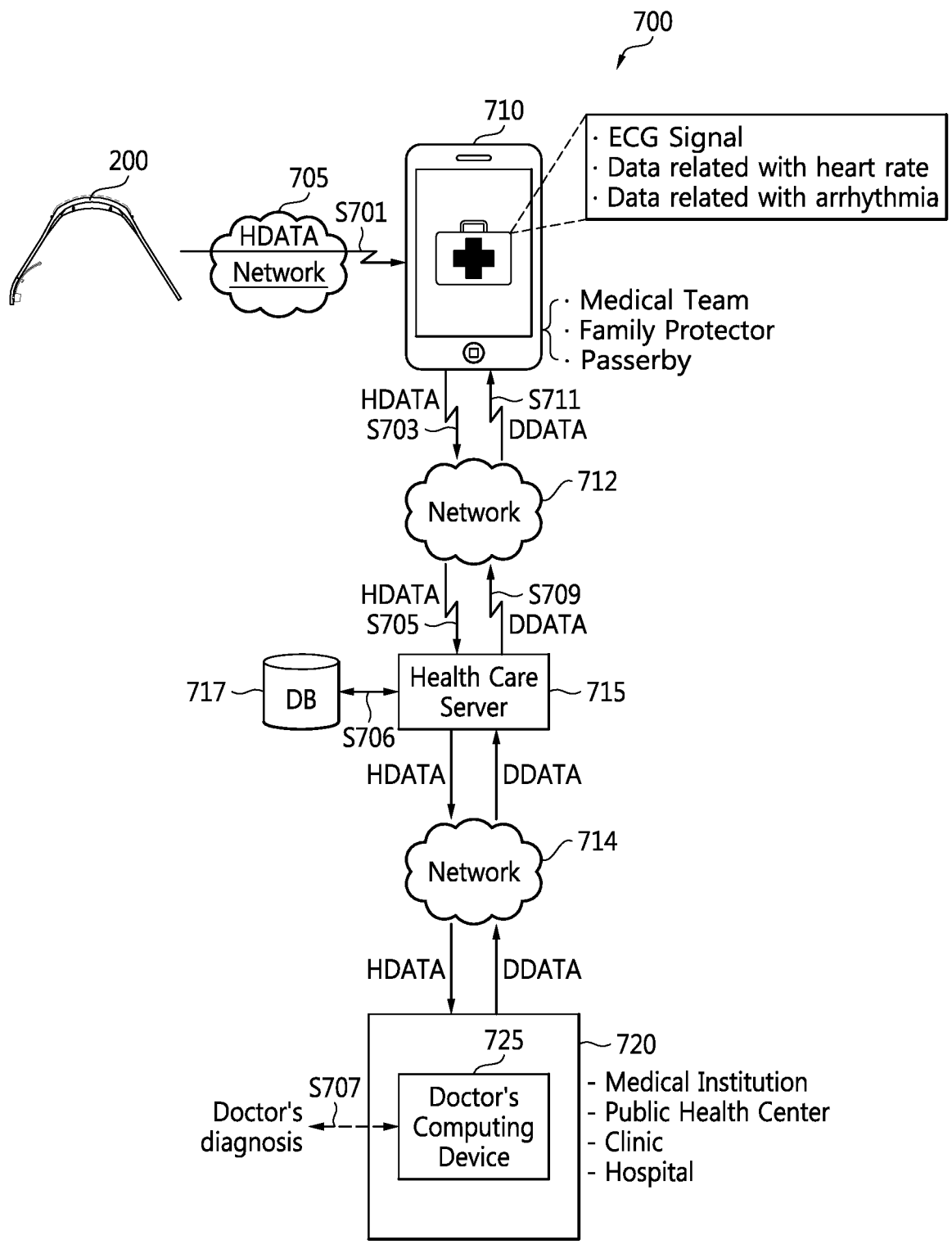
FIG. 18 is a block diagram of the health care system including the wearable device shown in FIG. 1.

FIG. 18 is a block diagram of another example of a data processing system including the wearable device shown in FIG. 1. Referring to FIGS. 1 to 12, and 18, a data processing system 700 may be used to provide a remote medical treatment. The data processing system 700 may include the wearable device 200 and a mobile computing device 710 for communicating with the wearable device 200 through a network 705. The data processing system 700 may further include a medical server 715 for communicating with the mobile computing device 710 through a network 712.

The wireless communication module 260 of the wearable device 200 may transmit data HDATA corresponding to biological data (for example, ECG data) to the mobile computing device 710 through the network 705 under the control of the bio-processor 230 or the application processor 275 (S701).

For example, the mobile computing device 710 may be a smart phone, a tablet PC, a mobile internet device (MID), an IoT device, or an internet of everything (IoE) device; however, it is not limited thereto. The user of the mobile computing device 710 may be a medical team, a family protector, or a passerby. The passerby may be one who has completed first aid training.

An application executed by a CPU of the mobile computing device 710 may display the data HDATA on a display device. The mobile computing device 710 may transmit the data HDATA to the medical server 715 through the network 712 under the control of the application (S703 and S705). The mobile computing device 710 stores a URL of the medical server 720, and thus transmits the data HDATA to the medical server 715 corresponding to the URL under the control of the application (S703 and S705).

The medical server 715 may store the data HDATA in a database 717 (S706), and transmit the data HDATA to a computing device 725 of a doctor working at a medical institution through a network 714.

The doctor may diagnose a state of health of a user wearing the wearable device 200 using the data HDATA displayed through the computing device 725 and input diagnosis data in the computing device 725 (S707). The computing device 725 may transmit the diagnosis data DDATA to the medical server 715 through the network 714, and the medical server 715 may store the diagnosis data DDATA in the database 717 (S706) and transmit the diagnosis data DDATA to the mobile computing device 710 through the network 712 (S709 and S711). The mobile computing device 710 may display the diagnosis data DDATA of the doctor on a display of the mobile computing device 710. Accordingly, a user of the mobile computing device 710 may perform appropriate medical care or first aid on the user wearing the wearable device 200 using the diagnosis data DDATA.

Figure 19:
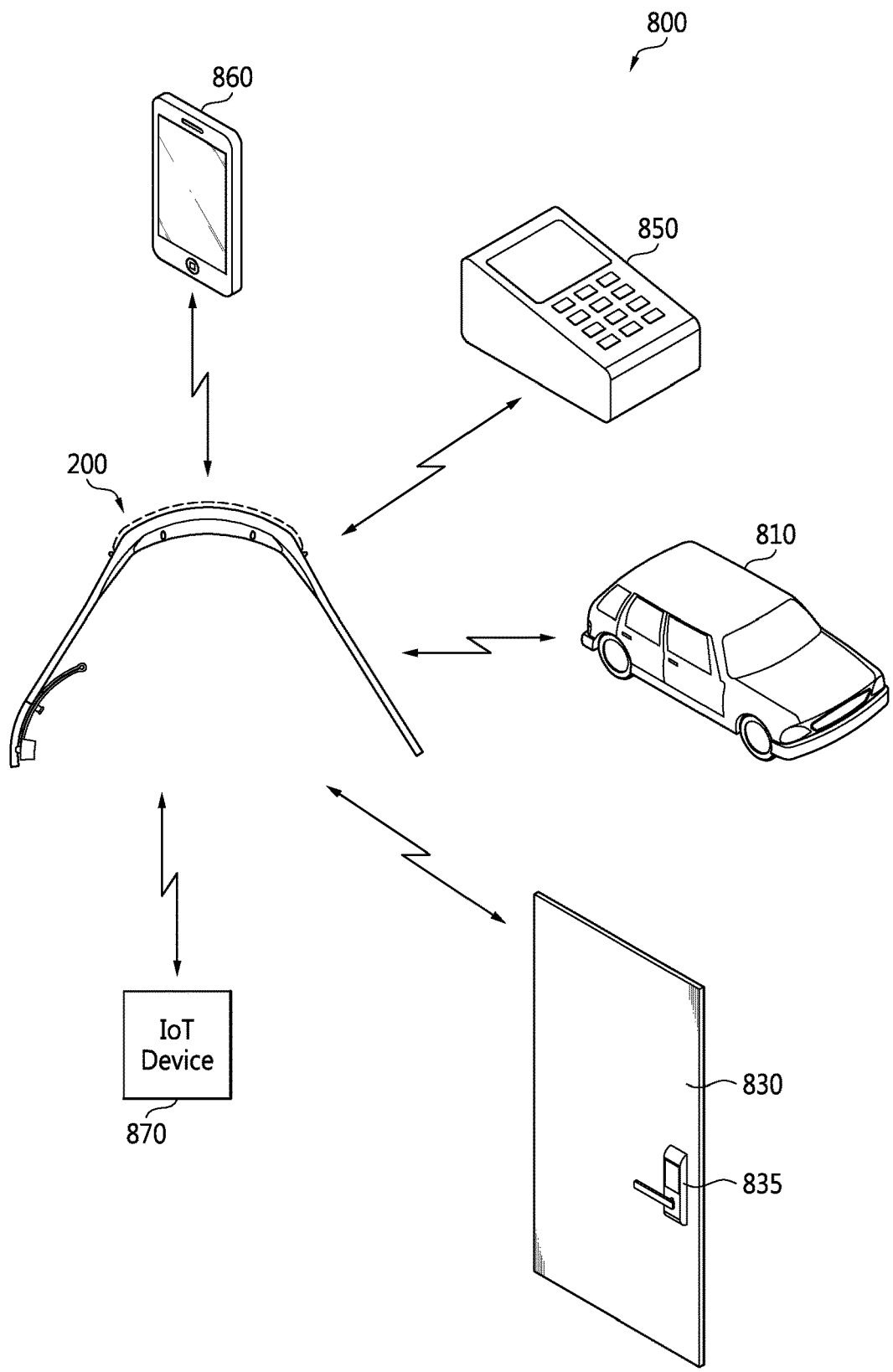
FIG. 19 is a block diagram of a security/authentication system including the wearable device shown in FIG. 1.
Figure 20:
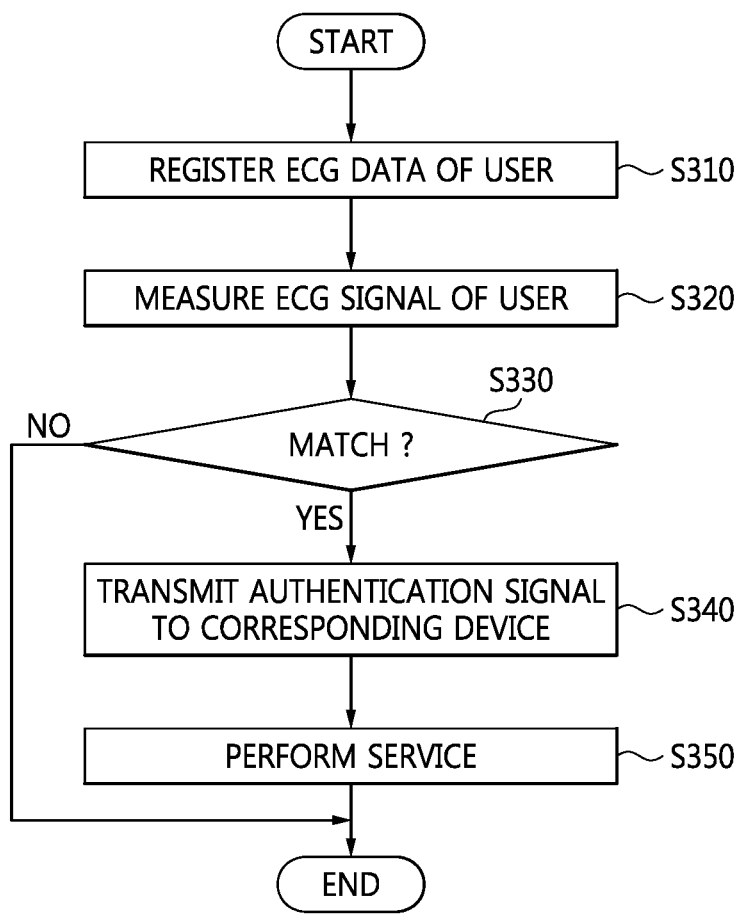
FIG. 20 is a flowchart for illustrating an operation of the security/authentication system shown in FIG. 19.

FIG. 19 is a block diagram of a security/authentication system 800 including the wearable device shown in FIG. 1, and FIG. 20 is a flowchart of an operation of the security/authentication system 800 shown in FIG. 19. An ECG signal among the biological signals (for example, an ECG signal, a BIA signal, and a GSR signal) differs from person to person, and thus may facilitate a mobile payment, security, or authentication.

Referring to FIGS. 1 to 12, 19, and 20, the wearable device 200 may be used as a device for making mobile payments, a device for a health solution, a device for a security solution, or a device for authentication.

The wearable device 200 may transmit or receive a wireless signal to or from an automobile 810, a digital door lock 835, a payment terminal 850, a smart phone 860, or an IoT device 870 using the wireless communication module 260.

According to examples, the bio-processor 230 or the application processor 275 of the wearable device 200 may execute a mobile payment application program (or software). User payment information for a mobile payment may be safely stored in a security region of the memory 255 under the control of the bio-processor 230 or the application processor 275. At this time, the user payment information may be encrypted and stored in the security region of the memory 255.

The mobile payment application program may perform a mobile payment with the payment terminal 850 using the user payment information stored in the security region of the memory 255. For example, the user payment information may include identification information (for example, credit card information, password, and ECG information) for identifying a genuine user of the wearable device 200. The identification information may be registered in the security region of the memory 255 through a mobile payment application program by the genuine user of the wearable device 200.

The bio-processor 230 may produce an ECG signal of the genuine user using the sensing electrodes 212 and 213 shown in FIG. 3 or 10, and store ECG data corresponding to the ECG signal in a security region of the memory 255 (S310). That is, the mobile payment application program may store the ECG data in the security region of the memory 255 (S310).

When a proprietor wants user authentication for a mobile payment, the bio-processor 230 may measure a biological signal, e.g., an ECG signal, using the sensing electrodes 212 and 213 shown in FIG. 3 or 10, and generate biological data BDATA, e.g., ECG data, corresponding to the ECG signal (S320).

A mobile payment application program executed by the bio-processor 230 or the DSP 232 may compare ECG data stored (or registered) in the security region of the memory 255 with ECG data generated by the DSP 232 (S320). When they are matched (Yes in S330), the mobile payment application program executed by the bio-processor 230 or the DSP 232 may generate an authentication signal which represents the match. According to an example, the mobile payment application program executed by the application processor 275 may compare ECG data stored (or registered) in the security region of the memory 255 with ECG data generated by the DSP 232, and generate an authentication signal (S330).

The authentication signal output from the bio-processor 230 or the application processor 275 may be transmitted to a device, for example, the payment terminal 850, through the wireless communication module 260 (S340). The payment terminal 850 may provide a user of the wearable device 200 with a mobile payment service (S350).

According to examples, the wearable device 200 may be used as a device for authenticating a user. Authentication information (for example, ECG data) for authenticating a user may be registered in the security region of the memory 255 by the bio-processor 230 or the application processor 275 (S310). As described above, the bio-processor 230 or the application processor 275 may compare ECG data stored (or registered) in the security region of the memory 255 at S310 with ECG data generated by the DSP 232 of the bio-processor 230 at S320 (S330), and generate an authentication signal according to a result of the comparison.

The authentication signal output from the bio-processor 230 or the application processor 275 may be transmitted to a corresponding device (for example, 810, 835, 860, or 870) through the wireless communication module 260 (S340).

A door key control device of the automobile 810 may unlock a door of the automobile 810 in response to the authentication signal. The digital door lock 835 installed in a door 830 may be unlocked in response to the authentication signal.

The smart phone 860 or the IoT device 870 requiring authentication or security may provide a service in response to the authentication signal. For example, the smart phone 860 may be connected to a charged website or perform a payment in response to the authentication signal. For example, when the IoT device 870 is a wireless access point, the wireless access point may connect the wearable device 200 to the internet in response to the authentication signal.

A processor according to an example of the present inventive concept can decide the number of pads or select the pads used to sense biological data, based on a selection signal indicating a type of biological information desired. Likewise, a wearable device including a plurality of electrodes according to an example of the present inventive concept can decide, based on a selection signal indicating a type of a biological information desired, a number of electrodes used to sense biological data and can enable or otherwise activate those electrodes for sensing the biological data.

That is, the wearable device including a plurality of electrodes can select, based on the selection signal, the number of electrodes to be used for each biological signal to be produced such that various biological signals can be produced using a limited number of electrodes. Accordingly, a user of the wearable device can conveniently measure each of various biological conditions anytime and anywhere. Furthermore, the wearable device is relatively compact considering the amount of biological data it can produce.

Although examples of the present general inventive concept have been shown and described, it will be appreciated by those skilled in the art that changes may be made in these examples without departing from the principles and spirit and scope of the general inventive concept as defined in the appended claims.

What is claimed is:

1. A wearable device comprising:
   a case wearable by a user of the device;
   a bio-processor embedded in the case; and
   a plurality of electrodes electrically connected to the bio-processor,
   wherein at least one electrode from among the plurality of electrodes is disposed at one side of the case to be in contact with a first part of the user wearing the device, and another electrode from among the plurality of electrodes is disposed at another side of the case so as to be exposed when the device is worn by the user,
   wherein the bio-processor is configured to decide, based on a selection signal indicating a type of user biological data desired, which ones of the plurality of electrodes to use as sensing electrodes for producing a biological signal from the user wearing the device,
   wherein the bio-processor is configured to decide, based on the selection signal, which ones of the plurality of electrodes to use, if any, as source electrodes for supplying current to the user wearing the device,
  wherein when the another electrode is used as one of the source electrodes based on the selection signal, the another electrode is in contact with a second part of the user, and
  wherein the first part of the user is spaced apart from the second part of the user.

2. The wearable device of claim 1, wherein the bio-processor includes:
  a plurality of current sources;
  a current source switch operatively connecting the plurality of current sources to at least some of the plurality of electrodes; and
  a controller operatively connected to the current source switch and configured to control the current source switch to selectively connect the plurality of current sources to respective ones of the electrodes in response to the selection signal.

3. The wearable device of claim 2, wherein the wearable device further includes a wireless communication module configured to transmit the selection signal from an external wireless device to the controller.

4. The wearable device of claim 1, wherein the bio-processor is configured to decide which of the plurality of electrodes to use as the sensing electrodes and which of the electrodes to use, if any, as the source electrodes in producing a biological signal of at least one of a bioelectrical impedance analysis (BIA), an electrocardiogram (ECG), and a galvanic skin response (GSR).

5. The wearable device of claim 4, wherein the bio-processor is configured to operate a same set of electrodes from among the plurality of electrodes as the sensing electrodes and the source electrodes to produce the biological signal of the galvanic skin response (GSR).

6. The wearable device of claim 4, wherein the case has a form of a wristband, and the at least one electrode is disposed at an inner side of the wristband so as to face a wrist of the user when the user is wearing the device.

7. The wearable device of claim 4, wherein the plurality of the electrodes comprise four electrodes, two electrodes from among the plurality of electrodes including the at least one electrode are disposed at the one side of the case, and two other electrodes from among the plurality of electrodes including the another electrode are disposed at the another side of the case and are spaced such that the two other electrodes can be pressed by a finger and thumb of one hand of the user, and
  the bio-processor is configured to operate the plurality of electrodes to produce the biological signal of the bioelectrical impedance analysis (BIA).

8. The wearable device of claim 1, wherein the bio-processor is configured to only operate electrodes from said plurality of electrodes as the sensing electrodes to produce the biological signal of an electrocardiogram (ECG), and includes:
  a controller configured to generate a switch control signal, designating which electrodes from among the plurality of electrodes are to serve as the sensing electrodes, in response to the selection signal, and
  voltage measuring circuitry configured to receive signals picked up by the electrodes designated as the sensing electrodes.

9. A wearable device comprising:
  a case;
  a bio-processor embedded in the case; and
  a plurality of electrodes operatively electrically connected to the bio-processor,
  wherein the bio-processor is configured to select a number of electrodes from among the plurality of electrodes as selected electrodes for use in sensing a state of a user wearing the device based on a selection signal corresponding to a type of biological signal to be generated as an indicator of the state, and is configured to enable the selected electrodes to sense the state and produce the biological signal, and
  the bio-processor comprises first and second current sources and is configured to selectively connect the first current source to a first pair of electrodes from among the plurality of electrodes when the type of biological signal to be generated is a bioelectrical impedance analysis (BIA) signal and connect the second current source to a second pair of electrodes from among the plurality of electrodes when the type of biological signal to be generated is a galvanic skin response (GSR) signal.

10. The wearable device of claim 9, wherein the bio-processor is configured to selectively generate as the biological signal the bioelectrical impedance analysis (BIA) signal, an electrocardiogram (ECG) signal, and the galvanic skin response (GSR) signal,
  the bio-processor is configured such that a number of the selected electrodes when the biological signal is the bioelectrical impedance analysis (BIA) signal is greater than a number of the selected electrodes when the biological signal is the electrocardiogram (ECG) signal, and
  the bio-processor is configured such that the number of the selected electrodes when the biological signal is the electrocardiogram (ECG) signal is equal to or greater than a number of the selected electrodes when the biological signal is the galvanic skin response (GSR) signal.

11. The wearable device of claim 9, wherein the bio-processor is configured to designate and operate each of the selected electrodes as a sensing electrode for sensing the state of the user and/or a source electrode for supplying current to an anatomical region of the user, and
  the bio-processor is configured to designate and operate each of the selected electrodes as both a sensing electrode and a source electrode when the biological signal is the galvanic skin response (GSR) signal, and to designate and operate each of the selected electrodes as only a sensing electrode or a source electrode when the biological signal is the bioelectrical impedance analysis (BIA) signal.

12. The wearable device of claim 9, wherein the first current source is configured to supply a sinusoidal wave signal as a current signal to the first pair of electrodes, and the second current source is configured to supply a pulse signal as a current signal to the second pair of electrodes.

13. A wearable device comprising:
  a casing securable to an anatomical region of a user of the device;
  a processor disposed within the casing;
  a power source integral with the casing; and
  at least three electrodes integral with the casing and electrically connected to the processor, and
  wherein the processor is operatively connected to the power source and to the electrodes and is configured to operate the device selectively in a plurality of different modes in response to mode selection signals input to the processor, respectively, and the modes include a first mode in which a first group of the electrodes is used to produce a bioelectrical impedance analysis (BIA) signal, a second mode in which a second group of the electrodes is used to produce a galvanic skin response (GSR) signal, and a third mode in which a third group of the electrodes is used to produce an electrocardiogram (ECG) signal, wherein at least one of the electrodes of the at least three electrodes is disposed on an outer side of the casing that is exposed when the device is worn by the user and is usable as a source electrode for supplying current to the user when contacted by the user.

14. The wearable device of claim 13, wherein the casing comprises a band, and the at least one of the electrodes is disposed at one side of the band and at least one other of the at least three electrodes is disposed at another side of the band such that each of the at least one other of the electrodes faces skin of the user when the device is worn, and each of the at least one electrodes can be pressed by a finger or thumb of the user.

15. The wearable device of claim 13, wherein the processor comprises:

a current switching circuit operatively connecting the at least three electrodes to the power source and operable to selectively electrically connect and disconnect each of respective ones of the at least three electrodes to and from the power source; and a voltage measuring circuit operable to measure a potential difference across respective ones of each of different pairs of the at least three electrodes.

16. The wearable device of claim 13, further comprising a wireless communication module integral with the casing and operatively connected to the processor, the wireless communication module enabling signals to be transmitted to and from the processor in a wireless manner.

17. The wearable device of claim 16, wherein the processor comprises a digital signal processor operatively connected to the at least three electrodes and to which the wireless communication module is operatively connected.

* * * * *